(12) United States Patent
Powell

(10) Patent No.: US 9,000,237 B2
(45) Date of Patent: Apr. 7, 2015

(54) ETHANOL REFINING PROCESS USING INTERMEDIATE REBOILER

(71) Applicant: Celanese International Corporation, Irving, TX (US)

(72) Inventor: Nathan Kirk Powell, Waxahachie, TX (US)

(73) Assignee: Celanese International Corporation, Irving, TX (US)

( * ) Notice: Subject to any disclaimer, the term of this patent is extended or adjusted under 35 U.S.C. 154(b) by 22 days.

(21) Appl. No.: 13/722,060

(22) Filed: Dec. 20, 2012

(65) Prior Publication Data

US 2014/0179957 A1    Jun. 26, 2014

(51) Int. Cl.
| | |
|---|---|
| *C07C 29/80* | (2006.01) |
| *C07C 29/74* | (2006.01) |
| *C07C 29/149* | (2006.01) |
| *C07C 29/147* | (2006.01) |

(52) U.S. Cl.
CPC .............. *C07C 29/80* (2013.01); *C07C 29/149* (2013.01); *C07C 29/74* (2013.01); *C07C 29/147* (2013.01)

(58) Field of Classification Search
USPC .......................................... 568/884, 885, 913
See application file for complete search history.

(56) References Cited

U.S. PATENT DOCUMENTS

| | | | |
|---|---|---|---|
| 1,469,447 A | 10/1923 | Schneible | |
| 2,549,416 A | 4/1951 | Brooks | |
| 2,591,671 A | 4/1952 | Catterall | |
| 2,591,672 A | 4/1952 | Catterall | |
| 2,607,719 A | 8/1952 | Eliot et al. | |
| 2,702,783 A | 2/1955 | Harrison et al. | |
| 2,715,604 A | 8/1955 | Weaver, Jr. | |
| 2,744,939 A | 5/1956 | Kennel | |
| 2,801,209 A | 7/1957 | Muller et al. | |
| 3,404,186 A | 10/1968 | Bailey et al. | |
| 3,408,267 A | 10/1968 | Miller et al. | |
| 3,445,345 A | 5/1969 | Katzen et al. | |
| 3,990,952 A | 11/1976 | Katzen et al. | |
| 4,306,942 A | 12/1981 | Brush et al. | |
| 4,319,058 A | 3/1982 | Kulprathipanja et al. | |
| 4,395,576 A | 7/1983 | Kwantes et al. | |
| 4,422,903 A | 12/1983 | Messick et al. | |
| 4,426,541 A | 1/1984 | King | |
| 4,448,644 A | 5/1984 | Foster et al. | |
| 4,454,358 A | 6/1984 | Kummer et al. | |
| 4,492,808 A | 1/1985 | Hagen et al. | |

(Continued)

FOREIGN PATENT DOCUMENTS

| | | |
|---|---|---|
| CN | 1230458 | 10/1999 |
| CN | 201768393 | 3/2011 |

(Continued)

OTHER PUBLICATIONS

International Search Report and Written Opinion for PCT/US213/077045 mailed Mar. 18, 2014.

(Continued)

*Primary Examiner* — Clinton Brooks
*Assistant Examiner* — Medhanit Bahta

(57) ABSTRACT

The present invention relates to processes for producing and recovering ethanol using an intermediate reboiler. An intermediate stream may be withdrawn from a removal zone of a distillation column and recirculated through the intermediate reboiler to the distillation column. The distillation column may also comprise a bottoms reboiler.

18 Claims, 4 Drawing Sheets

(56) References Cited

U.S. PATENT DOCUMENTS

| | | |
|---|---|---|
| 4,517,391 A | 5/1985 | Schuster et al. |
| 4,520,213 A | 5/1985 | Victor |
| 4,539,076 A | 9/1985 | Swain |
| 4,541,897 A | 9/1985 | Sommer et al. |
| 4,600,571 A | 7/1986 | McCarroll et al. |
| 4,626,321 A | 12/1986 | Grethlein et al. |
| 4,626,604 A | 12/1986 | Hiles et al. |
| 4,678,543 A | 7/1987 | Houben et al. |
| 4,761,505 A | 8/1988 | Diana et al. |
| 4,774,365 A | 9/1988 | Chen et al. |
| 4,842,693 A | 6/1989 | Wheldon |
| 4,880,937 A | 11/1989 | Matsushita et al. |
| 4,943,354 A | 7/1990 | Osterburg et al. |
| 5,035,776 A | 7/1991 | Knapp |
| 5,124,004 A | 6/1992 | Grethlein et al. |
| 5,149,680 A | 9/1992 | Kitson et al. |
| 5,185,481 A | 2/1993 | Muto et al. |
| 5,215,902 A | 6/1993 | Tedder |
| 5,250,271 A | 10/1993 | Horizoe et al. |
| 5,284,983 A | 2/1994 | Muto et al. |
| 5,346,593 A * | 9/1994 | Cialkowski et al. ............ 203/18 |
| 5,449,440 A | 9/1995 | Rescalli et al. |
| 5,488,185 A | 1/1996 | Ramachandran et al. |
| 5,565,068 A | 10/1996 | Parker et al. |
| 6,462,231 B1 | 10/2002 | Yanagawa et al. |
| 6,486,366 B1 | 11/2002 | Ostgard et al. |
| 6,495,730 B1 | 12/2002 | Konishi et al. |
| 6,509,180 B1 | 1/2003 | Verser et al. |
| 6,632,330 B1 | 10/2003 | Colley et al. |
| 6,809,217 B1 | 10/2004 | Colley et al. |
| 7,361,794 B2 | 4/2008 | Grosso |
| 7,399,892 B2 | 7/2008 | Rix et al. |
| 7,553,397 B1 | 6/2009 | Colley et al. |
| 7,572,353 B1 | 8/2009 | Vander et al. |
| 7,594,981 B2 | 9/2009 | Ikeda |
| 7,732,173 B2 | 6/2010 | Mairal et al. |
| 7,744,727 B2 | 6/2010 | Blum et al. |
| 7,790,938 B2 | 9/2010 | Kawasaki et al. |
| 7,842,844 B2 | 11/2010 | Atkins |
| 7,947,746 B2 | 5/2011 | Daniel et al. |
| 7,964,379 B2 | 6/2011 | Verser et al. |
| 8,002,953 B2 | 8/2011 | Lee et al. |
| 8,053,610 B2 | 11/2011 | Kikuchi et al. |
| 8,062,482 B2 | 11/2011 | Warner |
| 8,071,389 B2 | 12/2011 | Weck et al. |
| 8,088,832 B2 | 1/2012 | Melnichuk et al. |
| 8,128,826 B2 | 3/2012 | Plante et al. |
| 8,129,436 B2 | 3/2012 | Tirtowidjojo et al. |
| 8,198,057 B2 | 6/2012 | Padgett |
| 8,232,440 B2 | 7/2012 | Holtzapple et al. |
| 8,247,607 B2 | 8/2012 | Beavis et al. |
| 8,288,596 B2 | 10/2012 | Garton et al. |
| 8,299,132 B2 | 10/2012 | Gracey et al. |
| 8,299,133 B2 | 10/2012 | Gracey et al. |
| 8,329,436 B2 | 12/2012 | Verser et al. |
| 2007/0138083 A1 | 6/2007 | Aizawa |
| 2007/0144886 A1 | 6/2007 | Sylvester et al. |
| 2008/0135396 A1 | 6/2008 | Blum |
| 2009/0166172 A1 | 7/2009 | Casey et al. |
| 2010/0270139 A1 | 10/2010 | Halvorsen et al. |
| 2011/0004034 A1 | 1/2011 | Daniel et al. |
| 2011/0046421 A1 | 2/2011 | Daniel et al. |
| 2011/0190552 A1 * | 8/2011 | Powell et al. ................ 568/885 |
| 2011/0224462 A1 | 9/2011 | Ditzel et al. |
| 2012/0010438 A1 | 1/2012 | Lee et al. |
| 2012/0277495 A1 * | 11/2012 | Warner et al. ................ 568/885 |

FOREIGN PATENT DOCUMENTS

| | | |
|---|---|---|
| CN | 102091429 | 6/2011 |
| CN | 101525272 | 5/2012 |
| DE | 2723611 | 11/1978 |
| JP | 4-193304 | 7/1992 |
| JP | 2009-263356 | 11/2009 |
| JP | 2010-159212 | 7/2010 |
| WO | WO 83/03409 | 10/1983 |
| WO | WO 2008/135192 | 11/2008 |
| WO | WO 2009/009320 | 1/2009 |
| WO | WO 2009/009322 | 1/2009 |
| WO | WO 2009/009323 | 1/2009 |
| WO | WO2009/048335 A1 | 4/2009 |
| WO | WO 2012/149164 | 11/2012 |

OTHER PUBLICATIONS

Arnikar et al., "A gas chromatographic study of the kinetics of the uncatalysed esterification of acetic acid by ethanol," J. Chromatog. 47 (1970), p. 265-268.

Agrawal, "Thermally Coupled Distillation with Reduced Number of Intercolumn Vapor Transfers", AIChE Journal, vol. 46, No. 11, Nov. 2000, pp. 2198-2210.

* cited by examiner

ETHANOL REFINING PROCESS USING INTERMEDIATE REBOILER

FIELD OF THE INVENTION

The present invention relates generally to processes for producing and recovering alcohol and, in particular, to forming a crude ethanol composition and recovering ethanol from the crude ethanol composition. In particular, the recovery processes includes introducing a dilute acid stream to a distillation column, withdrawing an intermediate stream from the column, and recirculating the intermediate stream to the column through an intermediate reboiler.

BACKGROUND OF THE INVENTION

Ethanol for industrial use is conventionally produced from organic feed stocks, such as petroleum oil, natural gas, or coal, from feed stock intermediates, such as syngas, or from starchy materials or cellulose materials, such as corn or sugar cane. Conventional methods for producing ethanol from organic feed stocks, as well as from cellulose materials, include the acid-catalyzed hydration of ethylene, methanol homologation, direct alcohol synthesis, and Fischer-Tropsch synthesis. Instability in organic feed stock prices contributes to fluctuations in the cost of conventionally produced ethanol, making the need for alternative sources of ethanol production all the greater when feed stock prices rise. Starchy materials, as well as cellulose materials, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds, including esters, has been widely studied, and a variety of combinations of catalysts, supports, and operating conditions have been mentioned in the literature.

More recently, even though it may not still be commercially viable it has been reported that ethanol can be produced from hydrogenating acetic acid using a cobalt catalyst at superatmospheric pressures such as about 40 to 120 bar, as described in U.S. Pat. No. 4,517,391.

On the other hand, U.S. Pat. No. 5,149,680 describes a process for the catalytic hydrogenation of carboxylic acids and their anhydrides to alcohols and/or esters utilizing a platinum group metal alloy catalyst. The catalyst is comprised of an alloy of at least one noble metal of Group VIII of the Periodic Table and at least one metal capable of alloying with the Group VIII noble metal, admixed with a component comprising at least one of the metals rhenium, tungsten or molybdenum. Although it has been claimed therein that improved selectivity to a mixture of alcohol and its ester with the unreacted carboxylic acid is achieved over the prior art references it was still reported that 3 to 9 percent of alkanes, such as methane and ethane are formed as by-products during the hydrogenation of acetic acid to ethanol under their optimal catalyst conditions.

U.S. Pat. No. 5,284,983 describes a purification process for removing lipophilic impurities contained in an aqueous crude ethanol solution, particularly $C_3$-$C_4$ alcohols. The concentration-distillation column comprises ethanol and uses heat exchangers for both the residue and distillate.

U.S. Pat. No. 4,626,321 describes a method of distillation using a heat pump, which may be driven by a compressor, using vapor stream from within the distillation system as a heat source and a liquid stream from within the distillation system as a heat sink.

U.S. Pat. No. 5,346,593 teaches a methanol refining column and method using an intermediate reboiler to reduce methanol production energy requirements.

However, the conventional process for the purification of ethanol using a large number of distilling columns is very poor in energy efficiency.

The need remains for improved processes for efficient ethanol production by using heat integration on a commercially feasible scale.

SUMMARY OF THE INVENTION

In a first embodiment, the present invention is directed to a process for refining ethanol from a dilute acid stream, comprising: introducing the dilute acid stream to an inlet zone of a distillation column to yield an overhead comprising ethanol; recirculating an intermediate stream, withdrawn from a removal zone by passing the intermediate stream through an intermediate reboiler and returning the intermediate stream to the distillation column at or adjacent to the removal zone to supply heat to the distillation column, heating the distillation column below the removal zone with a bottoms reboiler and withdrawing a residue therefrom, wherein the residue comprises water and substantially all of the acid from the dilute acid stream; and recovering an ethanol product from the overhead. The composition of the intermediate stream may vary depending on the location of the removal zone within the distillation column. Generally, the composition of the intermediate stream has a boiling point that is less than boiling point of the residue. For example, the intermediate stream may have a boiling point that is 5% lower than a boiling point of the residue. In some embodiments, the intermediate stream may contain less ethanol based on weight than the dilute acid stream. Additionally, in the same or in alternative embodiments, the intermediate stream may be enriched in acid with respect to the dilute acid stream. The removal zone may be below the inlet zone. In other embodiments, the intermediate stream may be returned above the removal zone and/or above the inlet zone. The removal zone may be operated at a temperature above 80° C. The intermediate stream may be in the liquid phase and is heated using a heating medium comprising steam. The intermediate reboiler may be selected from the group consisting of an internal reboiler, a kettle reboiler, a jacketed kettle reboiler, a thermosyphon reboiler, a falling film reboiler, a fire reboiler and a forced circulation reboiler. The intermediate reboiler may provide from 5 to 60% of total heat to the distillation column and may be operated under non-esterification conditions, wherein substantially no ethyl acetate is formed in the intermediate reboiler. The bottoms reboiler may be selected from the group consisting of an internal reboiler, a kettle reboiler, a jacketed kettle reboiler, a thermosyphon reboiler, a falling film reboiler, a fire reboiler and a forced circulation reboiler. The ethanol product may comprise from 1 to 100 wppm acid, e.g., substantially no acid. The dilute acid stream may be substantially free of methanol and may comprise at least 0.1 wt. % acid, e.g., from 0.1 to 10 wt. % acid.

In a second embodiment, the present invention is directed to a process for refining ethanol, comprising: hydrogenating acetic acid and/or an ester thereof in a reactor in the presence of a catalyst to form a crude ethanol product; obtaining a dilute acid stream from the crude ethanol product that comprises a substantial portion of the ethanol from the crude ethanol product; introducing the dilute acid stream to an inlet zone of a distillation column to yield an overhead comprising ethanol; recirculating an intermediate stream, withdrawn from a removal zone, by passing the intermediate stream through an intermediate reboiler and returning the intermediate stream to the distillation column at or adjacent to the removal zone to supply heat to the distillation column, heating the distillation column below the removal zone with a bottoms reboiler and withdrawing a residue therefrom; and recovering an ethanol product from the overhead. The composition of the intermediate stream may vary depending on the location of the removal zone within the distillation column. Generally, the composition of the intermediate stream has a boiling point that is less than boiling point of the residue. For example, the intermediate stream may have a boiling point that is 5% lower than a boiling point of the residue. In some embodiments, the intermediate stream may contain less ethanol based on weight than the dilute acid stream. Additionally, in the same or in alternative embodiments, the intermediate stream may be enriched in acid with respect to the dilute acid stream. The residue may comprise water and substantially all of the acetic acid from the dilute acid stream. The removal zone may be below the inlet zone. In other embodiments, the intermediate stream may be returned above the removal zone and/or above the inlet zone. The removal zone may be operated at a temperature above 80° C. The intermediate stream may be in the liquid phase and is heated using a heating medium comprising steam. The intermediate reboiler may be selected from the group consisting of an internal reboiler, a kettle reboiler, a jacketed kettle reboiler, a thermosyphon reboiler, a falling film reboiler, a fire reboiler and a forced circulation reboiler. The intermediate reboiler may provide from 5 to 60% of total heat to the distillation column and may be operated under non-esterification conditions, wherein substantially no ethyl acetate is formed in the intermediate reboiler. The bottoms reboiler may be selected from the group consisting of an internal reboiler, a kettle reboiler, a jacketed kettle reboiler, a thermosyphon reboiler, a falling film reboiler, a fire reboiler and a forced circulation reboiler. The ethanol product may comprise from 1 to 100 wppm acid, e.g., substantially no acid. The dilute acid stream may be substantially free of methanol and may comprise at least 0.1 wt. % acid, e.g., from 0.1 to 10 wt. % acid. The acetic acid may be formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

In a third embodiment, the present invention is directed to a process for refining ethanol from a dilute acid stream, comprising: hydrogenating acetic acid and/or an ester thereof in a reactor in the presence of a catalyst to form a crude ethanol product; separating at least a portion of the crude ethanol product in a first distillation column to yield a first distillate comprising ethanol, ethyl acetate and water and a first residue comprising acetic acid; separating at least a portion of the first distillate in a second distillation column to yield a second distillate comprising ethyl acetate and a second residue comprising ethanol and water; separating at least a portion of the second residue in a third distillation column by introducing the second residue to an inlet zone of the third distillation column to yield an overhead comprising ethanol; recirculating an intermediate stream, withdrawn from a removal zone, by passing the intermediate stream through an intermediate reboiler and returning the intermediate stream to the third distillation column at or adjacent to the removal zone to supply heat to the third distillation column; heating the distillation column below the removal zone with a bottoms reboiler and withdrawing a third residue therefrom comprising water; and recovering an ethanol product from the overhead. The removal zone may be below the inlet zone. In other embodiments, the intermediate stream may be returned above the removal zone and/or above the inlet zone. The removal zone may be operated at a temperature above 80° C. The intermediate stream may be in the liquid phase and is heated using a heating medium comprising steam. The composition of the intermediate stream has a boiling point that is less than boiling point of the residue. For example, the intermediate stream may have a boiling point that is 5% lower than a boiling point of the residue. The intermediate reboiler may be selected from the group consisting of an internal reboiler, a kettle reboiler, a jacketed kettle reboiler, a thermosyphon reboiler, a falling film reboiler, a fire reboiler and a forced circulation reboiler. The intermediate reboiler may provide from 5 to 60% of total heat to the distillation column and may be operated under non-esterification conditions, wherein substantially no ethyl acetate is formed in the intermediate reboiler. The bottoms reboiler may be selected from the group consisting of an internal reboiler, a kettle reboiler, a jacketed kettle reboiler, a thermosyphon reboiler, a falling film reboiler, a fire reboiler and a forced circulation reboiler. The ethanol product may comprise from 1 to 100 wppm acid, e.g., substantially no acid. The dilute acid stream may be substantially free of methanol and may comprise at least 0.1 wt. % acid, e.g., from 0.1 to 10 wt. % acid. The acetic acid may be formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

In a fourth embodiment, the present invention is directed to a process for refining ethanol from a dilute acid stream, comprising: hydrogenating acetic acid and/or an ester thereof in a reactor in the presence of a catalyst to form a dilute acid stream; introducing the dilute acid stream to an inlet zone of a first distillation column to yield a first distillate comprising ethanol, ethyl acetate and water; recirculating an intermediate stream, withdrawn from a removal zone, by passing the intermediate stream through an intermediate reboiler and returning the intermediate stream to the first distillation column at or adjacent to the removal zone to supply heat to the first distillation column; heating the distillation column below the removal zone with a bottoms reboiler and withdrawing a first residue therefrom comprising water and acetic acid; and separating the first distillate in a second distillation column to form a second distillate comprising ethyl acetate and water and a second residue comprising ethanol. In some embodiments, the first distillate may be passed through a water removal unit prior to being fed to the second distillation column. The removal zone may be below the inlet zone. In other embodiments, the intermediate stream may be returned above the removal zone and/or above the inlet zone. The removal zone may be operated at a temperature above 80° C. The intermediate stream may be in the liquid phase and is heated using a heating medium comprising steam. The composition of the intermediate stream has a boiling point that is less than boiling point of the residue. For example, the intermediate stream may have a boiling point that is 5% lower than a boiling point of the residue. The intermediate reboiler may be selected from the group consisting of an internal reboiler, a kettle reboiler, a jacketed kettle reboiler, a thermosyphon reboiler, a falling film reboiler, a fire reboiler and a forced circulation reboiler. The intermediate reboiler may provide from 5 to 60% of total heat to the distillation column and may be operated under non-esterification conditions, wherein substantially no ethyl acetate is formed in the intermediate reboiler. The bottoms reboiler may be selected from the group consisting of an internal reboiler, a kettle reboiler, a jacketed kettle reboiler, a thermosyphon reboiler, a falling film reboiler, a fire reboiler and a forced circulation reboiler. The ethanol product may comprise from 1 to 100 wppm acid, e.g., substantially no acid. The dilute acid stream may be substantially free of methanol and may comprise at least 0.1 wt. % acid, e.g., from 0.1 to 10 wt. % acid. The acetic acid may be formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

In a fifth embodiment, the present invention is directed to a process for refining ethanol from a dilute acid stream, comprising: hydrogenating acetic acid and/or an ester thereof in a reactor in the presence of a catalyst to form a crude ethanol product; separating at least a portion of the crude ethanol product in a first distillation column to yield a first distillate comprising ethyl acetate and acetaldehyde and a first residue comprising a dilute acid stream; introducing the dilute acid stream to an inlet zone of a second distillation column to yield a second distillate comprising ethanol and ethyl acetate; recirculating an intermediate stream, withdrawn from a removal zone, by passing the intermediate stream through an intermediate reboiler and returning the intermediate stream to the second distillation column at or adjacent to the removal zone to supply heat to the second distillation column; heating the distillation column below the removal zone with a bottoms reboiler and withdrawing a second residue therefrom comprising water and acetic acid; and separating the second distillate in a third distillation column to form a third distillate comprising ethyl acetate and a third residue comprising ethanol. At least a portion of the third distillate may be returned the first distillation column. The removal zone may be below the inlet zone. In other embodiments, the intermediate stream may be returned above the removal zone and/or above the inlet zone. The removal zone may be operated at a temperature above 80° C. The intermediate stream may be in the liquid phase and is heated using a heating medium comprising steam. The composition of the intermediate stream has a boiling point that is less than boiling point of the residue. For example, the intermediate stream may have a boiling point that is 5% lower than a boiling point of the residue. The intermediate reboiler may be selected from the group consisting of an internal reboiler, a kettle reboiler, a jacketed kettle reboiler, a thermosyphon reboiler, a falling film reboiler, a fire reboiler and a forced circulation reboiler. The intermediate reboiler may provide from 5 to 60% of total heat to the distillation column and may be operated under non-esterification conditions, wherein substantially no ethyl acetate is formed in the intermediate reboiler. The bottoms reboiler may be selected from the group consisting of an internal reboiler, a kettle reboiler, a jacketed kettle reboiler, a thermosyphon reboiler, a falling film reboiler, a fire reboiler and a forced circulation reboiler. The ethanol product may comprise from 1 to 100 wppm acid, e.g., substantially no acid. The dilute acid stream may be substantially free of methanol and may comprise at least 0.1 wt. % acid, e.g., from 0.1 to 10 wt. % acid. The acetic acid may be formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

BRIEF DESCRIPTION OF DRAWINGS

The invention may be more completely understood in consideration of the following detailed description of various embodiments of the invention in connection with the accompanying drawings, wherein like numerals designate similar parts.

DETAILED DESCRIPTION OF THE INVENTION

Introduction

Figure 1:
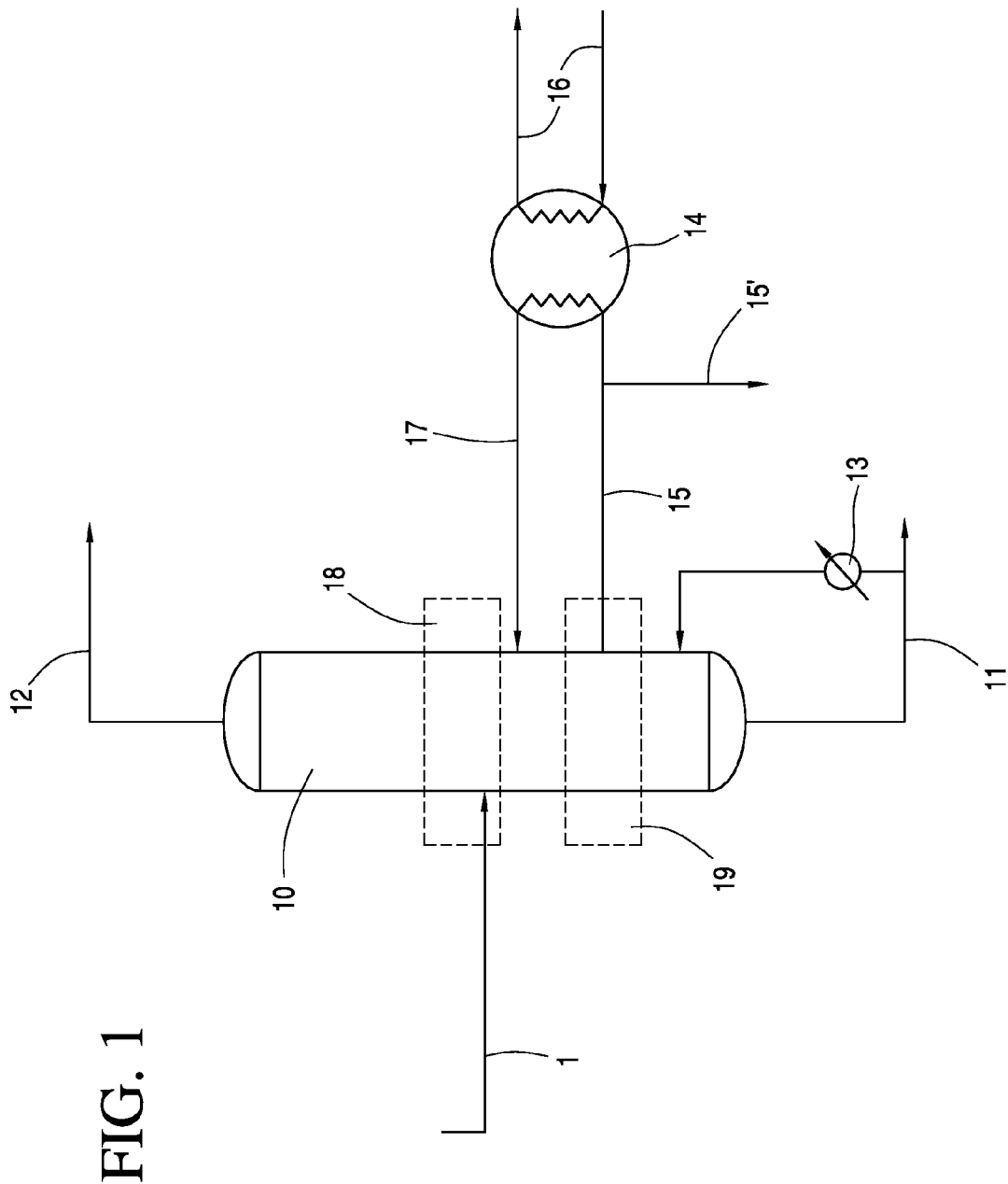
FIG. 1 is a schematic diagram of a distillation column with an intermediate reboiler in accordance with one embodiment of the present invention.

The present invention relates generally to processes for producing, separating and refining ethanol. In particular the process is directed to processes for refining ethanol obtained by hydrogenating acetic acid and/or esters thereof. For these processes, there are two problems: that water may be produced in an equal molar ratio with ethanol, and that there may be residual acetic acid due to low conversion of acetic acid. Water is difficult to completely remove from ethanol using distillation columns and requires a significant amount of energy. Also, depending on the catalyst, there may be a low conversion of acetic acid but a high selectivity to ethanol. Thus, there is residual or unreacted acetic acid that must be separated from the crude ethanol product. The presence of the acetic acid in the crude ethanol product may lead to further reduction of the ethanol through esterification. Any acetic acid that is carried over in the ethanol product may affect the pH and resulting in undesirable properties for the ethanol.

The present invention advantageously overcomes these problems in separating ethanol and water by using a distillation column having an intermediate and bottoms reboiler. The intermediate reboiler or side-reboiler may advantageously reduce the total energy requirement of the distillation column. In addition, the intermediate reboiler does not operate under conditions that significantly convert any acetic acid present to esters. Further the intermediate reboiler concentrates any acetic acid present in the column in the water stream instead of the ethanol stream.

An intermediate reboiler may also be used when the liquid/vapor ratio in a rectification zone of a distillation column limits separation and where the liquid/vapor ratio in a stripping zone is not limiting. Without being bound by theory, the intermediate reboiler, while not changing the liquid/vapor ratio in the rectification zone, may be used to reduce the liquid/vapor ratio in the stripping zone. This may reduce the tendency of components in the dilute acid feed to bulge in the stripping zone.

In one embodiment, the present invention is directed to refining ethanol from a dilute acid stream. As explained herein, the ethanol may be formed from the hydrogenation of an alkanoic acid, e.g., acetic acid, or an ester thereof. The acid in the dilute acid stream may be acetic acid. The dilute acid steam comprises at least 0.1 wt. % acid, e.g., at least 0.5 wt. % acid or at least 1 wt. % acid. In terms of ranges, the dilute acid stream may comprise from 0.01 to 30 wt. % acetic acid, e.g., from 0.1 to 10 wt. % or 0.5 to 5 wt. % acetic acid. In some embodiments, the dilute acid stream is substantially free of methanol, e.g., free of methanol. The dilute acid stream may have been subjected to light ends removal, including removal of ethyl acetate, acetaldehyde, and/or inert or reactant gases, e.g., hydrogen.

In another embodiment, the present invention is directed to refining an ethanol-water stream obtained from the crude product from the hydrogenation of acetic acid and/or esters thereof. Preferably, the acetic acid in the crude ethanol product is removed prior to separating the ethanol-water stream.

As shown in FIG. 1, a dilute acid stream in line 1 is fed to an inlet zone 18 of distillation column 10. Distillation column 10 comprises inlet zone 18 and removal zone 19. The inlet and/or removal zones may be used to separate the rectification zone and stripping zone. An overhead stream comprising an ethanol product in line 12 is removed from the column and may be recovered or directed to further separation processes. In some embodiments, the ethanol product comprises substantially no acid, e.g., acetic acid. In terms of ranges, the ethanol product may comprise from 0.1 to 500 wppm acid, e.g., from 1 to 100 wppm acid or from 1 to 50 wppm acid.

Intermediate stream in line 15 is withdrawn from removal zone 19 and is recirculated to distillation column 10 at or adjacent to removal zone 19 to supply heat to distillation column 10. In one embodiment, a hat tray may be used to build up liquid in removal zone 19 to remove intermediate stream in line 15. Intermediate stream 15 may be in the liquid phase. At least a portion of intermediate stream 15 may be purged via line 15'. The remainder of intermediate stream 15 is passed through intermediate reboiler 14 where it is vaporized and returned to distillation column 10 via line 17 in vapor phase. Intermediate stream 15 may be heated using a heating medium provided to intermediate reboiler 14 via lines 16. The heating medium may be generated within the ethanol production and recovery process or may be from an external source. In some embodiments, the heating medium is steam.

Intermediate stream is returned via line 17 to distillation column 10 above removal zone 19 and/or above inlet zone 18. In some embodiments, intermediate stream may be returned near inlet zone 18. In other embodiments, intermediate stream in line 17 may be returned to distillation column 10 below removal zone 19 (not shown). In some embodiments, the removal zone may be at the same level as the inlet zone (not shown) or above the inlet (not shown). The removal zone may be operated at a temperature above 70° C., e.g., above 80° C. or above 90° C. The determination of where the intermediate stream may be returned may depend on the temperature of the intermediate zone, the temperature of the removal zone, the components of the dilute acid stream and the components of the intermediate stream.

A residue is withdrawn from distillation column 10 via line 11 and is passed through a bottoms reboiler 13. The residue is then returned to distillation column 10 below removal zone 19.

The intermediate reboiler may be selected from the group consisting of an internal reboiler, a kettle reboiler, a jacketed kettle reboiler, a thermosyphon reboiler, a falling film reboiler, a fire reboiler, and a forced circulation reboiler. The intermediate reboiler may supply at least 5% of the total heat used by the distillation column, e.g., at least 10% or at least 20%. In terms of ranges, the intermediate reboiler may supply from 5 to 60% of the total heat used by the distillation column, e.g., from 10 to 45% or from 15 to 35%.

The heat source for the intermediate reboiler may be an external source or may come from within the process. As discussed herein, the heat source may be steam. This steam may be steam that is integrated from carbonylation of acetic acid. In some embodiments, the steam may be low quality acid, e.g., steam with a pressure of less than 600 kPa. Suitable steam generators may include a shell and tube exchanger, double pipe exchanger, spiral plate exchanger, plate heat exchanger, helical coil, spiral coil or bayonet tube in tank heat changer, or any other suitable heat exchanger known in the art. The process side of the steam generator can be comprised of any suitable material known in the art, for example a nickel-molybdenum alloy such as HASTELLOY™ B-3 alloy (Haynes International) or a zirconium alloy such as Zirc™ 702 alloy (United Titanium Inc.). The steam (water) side of the steam generator can be comprised of any suitable metal, including carbon steel and lower grade stainless and alloy steels.

In other embodiments, the heat source for the intermediate reboiler may be obtained from a hot condensate from within the reaction/separation process. This hot condensate may originate from any vaporized stream in the process, including the blowdown stream and the overhead from the vaporizer.

The intermediate reboiler may be operated under non-esterification conditions, e.g., conditions wherein substantially no ethyl acetate, e.g. less than 1000 ppm is formed in the intermediate stream as it passes through the reboiler. These conditions may include, but are not limited to, maintaining a minimum temperature for the intermediate stream and controlling residence time of the intermediate stream in the reboiler. Therefore, the ethyl acetate concentration of the intermediate stream in the liquid phase, prior to passing through the intermediate reboiler, and in the vapor phase, after passing through the intermediate reboiler, is substantially the same.

In some embodiments, the intermediate stream may contain less ethanol, on a weight basis, than the dilute acid stream fed to the column. For example, the intermediate stream may contain less than 30 wt. % ethanol, e.g., less than 25 wt. % or less than 15 wt. %. The intermediate stream may be enriched in acid, on a weight basis, as compared to the dilute acid stream. For example, the intermediate stream may contain more than 1 wt. % acetic acid, e.g., more than 3 wt. % or more than 5 wt. %. It is understood that the composition of the intermediate stream is dependent upon where the removal zone is located.

The intermediate stream may have a lower boiling point than the residue stream. In some embodiments, the lower boiling point may be 5% lower than the boiling point of the residue, e.g., 10% lower or 15% lower. In some embodiments, the boiling point of the intermediate stream may be at least 5° C. lower than the residue, e.g., at least 10° C. lower or at least 15° C. lower.

The distillation column may also be heated below the removal zone with a bottoms reboiler. A residue may be withdrawn from the bottom of the distillation column and passed through the bottoms reboiler. The residue may comprise water and may further comprise substantially all of the acid that was present in the dilute acid stream.

The bottoms reboiler may be selected from the group consisting of an internal reboiler, a kettle reboiler, a jacketed kettle reboiler, a thermosyphon reboiler, a falling film reboiler, a fire reboiler, and a forced circulation reboiler. The bottoms reboiler may supply at least 40% of the total heat used by the distillation column, e.g., at least 50% or at least 60%. In terms of ranges, the bottoms reboiler may supply from 40 to 95% of the total heat used by the distillation column, e.g., from 50 to 90% or from 55 to 85%. The bottoms reboiler is generally a dedicated utility reboiler. Reducing the load on the bottom reboiler by using an intermediate reboiler, as described herein, may allow different heat mediums to be used for the bottoms reboiler. As explained above, the heat medium may be steam or hot condensate from streams within the reaction and separation processes.

In another embodiment, the process is directed to a process for refining ethanol comprising hydrogenating acetic acid and/or an ester thereof in a reactor in the presence of a catalyst to form a crude ethanol product. The process further comprises obtaining a dilute acid stream from the crude ethanol product, wherein the dilute acid stream comprises a substantial portion of the ethanol from the crude ethanol product. The dilute acid steam comprises at least 0.1 wt. % acid, e.g., at least 0.5 wt. % acid or at least 1 wt. % acid. In terms of ranges, the dilute acid stream may comprise from 0.01 to 30 wt. % acetic acid, e.g., from 0.1 to 10 wt. % or 0.5 to 5 wt. % acetic acid. In some embodiments, the dilute acid stream is substantially free of methanol, e.g., free of methanol. The dilute acid stream may have been subjected to light ends removal, including removal of ethyl acetate, acetaldehyde, and/or inert or reactant gases, e.g., hydrogen.

The dilute acid stream may be introduced to an inlet zone of a distillation column where it is separated to yield an overhead comprising ethanol. A finished ethanol product may be recovered from the overhead.

An intermediate stream is withdrawn from a removal zone and recirculated to the column by passing the intermediate stream through an intermediate reboiler. The intermediate stream is returned to the distillation column at or adjacent to the removal zone. As explained herein, the location of the removal zone, inlet zone, and return of the intermediate stream may be varied, depending on numerous considerations, including the desired separation, the liquid/vapor ratio in the rectification zone, the boiling points of the intermediate stream and residue, and the compositions of the intermediate stream and residue.

In yet another embodiment, the present invention is directed to a process for refining ethanol from a dilute acid stream, comprising hydrogenating acetic acid and/or an ester thereof in a reactor in the presence of a catalyst to form a crude ethanol product. The process may further comprise separating at least a portion of the crude ethanol product in a first distillation column to yield a first distillate comprising ethanol, ethyl acetate and water and a first residue comprising acetic acid. At least a portion of the first distillate may be separated in a second distillation column to yield a second distillate comprising ethyl acetate and a second residue comprising ethanol and water. At least a portion of the second residue may be separated in a third distillation column by introducing the second residue to an inlet zone of the third distillation column to yield an overhead comprising ethanol. An intermediate stream, withdrawn from a removal zone, may be recirculated to the third distillation column by passing the intermediate stream through an intermediate reboiler and returning the intermediate stream to the third distillation column at or adjacent to the removal zone to supply heat to the third distillation column. Additional heat may be supplied to the distillation column by withdrawing a third residue comprising water from the third distillation column. The third residue is withdrawn from the column below the removal zone and is passed through a bottoms reboiler as described herein. A finished ethanol product may be recovered from the third distillate, also referred to as an overhead from the third distillation column.

Hydrogenation of Acetic Acid

The process of the present invention may be used with any hydrogenation process for producing ethanol. The materials, catalysts, reaction conditions, and separation processes that may be used in the hydrogenation of acetic acid are described further below.

The raw materials, acetic acid and hydrogen, fed to the reactor used in connection with the process of this invention may be derived from any suitable source including natural gas, petroleum, coal, biomass, and so forth. As examples, acetic acid may be produced via methanol carbonylation, acetaldehyde oxidation, ethane oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

Biomass-derived syngas has a detectable $^{14}C$ isotope content as compared to fossil fuels such as coal or natural gas. An equilibrium forms in the Earth's atmosphere between constant new formation and constant degradation, and so the proportion of the $^{14}C$ nuclei in the carbon in the atmosphere on Earth is constant over long periods. The same distribution ratio $n^{14}C:n^{12}C$ ratio is established in living organisms as is present in the surrounding atmosphere, which stops at death and $^{14}C$ decomposes at a half life of about 6000 years. Methanol, acetic acid and/or ethanol formed from biomass-derived syngas would be expected to have a $^{14}C$ content that is substantially similar to living organisms. For example, the $^{14}C$:$^{12}C$ ratio of the methanol, acetic acid and/or ethanol may be from one half to about 1 of the $^{14}C$:$^{12}C$ ratio for living organisms. In other embodiments, the syngas, methanol, acetic acid and/or ethanol described herein are derived wholly from fossil fuels, i.e. carbon sources produced over 60,000 years ago, may have no detectable $^{14}C$ content.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal sewage, municipal garbage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form syngas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into syngas, and U.S. Pat. No. 6,685,754, which discloses a method for the production of a hydrogen-containing gas composition, such as syngas including hydrogen and carbon monoxide, are incorporated herein by reference in their entireties.

The acetic acid feed to the hydrogenation reactor may also comprise other carboxylic acids and anhydrides, as well as aldehyde and/or ketones, such as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. In accordance with embodiments of the present invention, water may also be present in the acetic acid feed. Preferably, the feed to the hydrogenation reactor does not comprise syngas or a mixture of hydrogen, carbon monoxide, and/or carbon dioxide that would be similar to syngas. In other embodiments, the feed to the hydrogenation reactor does not contain alkanes including linear or cyclic alkane, such as ethane and/or cyclohexane.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the hydrogenation reactor without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

Some embodiments of the process of hydrogenating acetic acid to form ethanol may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed as the reactor, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation in the reactor may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The reactor pressure may range from 10 kPa to 3000 kPa, e.g., from 50 kPa to 2300 kPa, or from 100 kPa to 1500 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^-$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 18:1 to 2:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, from 0.1 to 100 seconds, e.g., from 0.3 to 80 seconds or from 0.4 to 30 seconds.

The hydrogenation of acetic acid to form ethanol is preferably conducted in the presence of a hydrogenation catalyst in the reactor. The hydrogenation catalyst is preferably a bifunctional catalyst and may convert acetic acid and ethyl acetate. The catalysts preferably are not methanol synthesis catalysts and are substantially free of copper and/or zinc, including oxides thereof. Suitable hydrogenation catalysts include catalysts comprising a first metal and optionally one or more of a second metal, a third metal or any number of additional metals, optionally on a catalyst support. Preferred bimetallic combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, nickel/palladium, gold/palladium, ruthenium/rhenium, and ruthenium/iron. Additional metal combinations may include palladium/rhenium/tin, palladium/rhenium/cobalt, palladium/rhenium/nickel, platinum/tin/palladium, platinum/tin/cobalt, platinum/tin/chromium, and platinum/tin/nickel.

The hydrogenation of acetic acid to form ethanol is preferably conducted in the presence of a hydrogenation catalyst. Exemplary catalysts are further described in U.S. Pat. Nos. 7,608,744 and 7,863,489, and U.S. Pub. Nos. 2010/0121114 and 2010/0197985, the entireties of which are incorporated herein by reference. In another embodiment, the catalyst comprises a Co/Mo/S catalyst of the type described in U.S. Pub. No. 2009/0069609, the entirety of which is incorporated herein by reference. In some embodiments the catalyst may be a bulk catalyst.

In one embodiment, the catalyst comprises a first metal selected from the group consisting of iron, cobalt, nickel, ruthenium, rhodium, palladium, osmium, iridium, platinum, titanium, chromium, rhenium, molybdenum, and tungsten. Preferably, the first metal is selected from the group consisting of platinum, palladium, cobalt, nickel, and ruthenium. More preferably, the first metal is selected from platinum and palladium. In embodiments of the invention where the first metal comprises platinum, it is preferred that the catalyst comprises platinum in an amount less than 5 wt. %, e.g., less than 3 wt. % or less than 1 wt. %, due to the high commercial demand for platinum.

As indicated above, in some embodiments, the catalyst further comprises a second metal, which typically would function as a promoter. If present, the second metal preferably is selected from the group consisting of molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 7.5 wt. %. For catalysts comprising two or more metals, the two or more metals may be alloyed with one another or may comprise a non-alloyed metal solution or mixture.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, platinum, tin, and rhenium. More preferably, the third metal is selected from cobalt, palladium, and ruthenium. When present, the total weight of the third metal preferably is from 0.1 to 20 wt. %, e.g., from 0.1 to 10 wt. %, or from 0.1 to 7.5 wt. %. In one embodiment, the catalyst may comprise platinum, tin and cobalt.

In addition to one or more metals, in some embodiments of the present invention the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 99 wt. %, or from 80 to 97.5 wt. %. In preferred embodiments that utilize a modified support, the support modifier is present in an amount from 0.1 to 50 wt. %, e.g., from 0.2 to 25 wt. %, from 1 to 20 wt. %, or from 3 to 15 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

Suitable support materials may include, for example, stable metal oxide-based supports or ceramic-based supports. Preferred supports include silicaceous supports, such as silica, silica gel, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

As indicated, the catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $Co_2O_3$, and $Bi_2O_3$.

In another embodiment, the support modifier may be a basic modifier that has a low volatility or no volatility. Such basic modifiers, for example, may be selected from the group consisting of: (i) alkaline earth metal oxides, (ii) alkali metal oxides, (iii) alkaline earth metal metasilicates, (iv) alkali metal metasilicates, (v) Group IIIB metal oxides, (vi) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium and yttrium, as well as mixtures of any of the foregoing. More preferably, the basic support modifier is a calcium silicate, and even more preferably calcium metasilicate ($CaSiO_3$). The calcium metasilicate may be crystalline or amorphous.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197985 referred to above, the entireties of which are incorporated herein by reference.

After the washing, drying and calcining of the catalyst is completed, the catalyst may be reduced in order to activate the catalyst. Reduction is carried out in the presence of a reducing gas, preferably hydrogen. The reducing gas is continuously passed over the catalyst at an initial ambient temperature that is increased up to 400° C. In one embodiment, the reduction is preferably carried out after the catalyst has been loaded into the reaction vessel where the hydrogenation will be carried out.

In particular, the hydrogenation of acetic acid may achieve favorable conversion of acetic acid and ethyl acetate, and favorable selectivity and productivity to ethanol. For purposes of the present invention, the term "conversion" refers to the amount of acetic acid or ethyl acetate in the feed that is converted to a compound other than acetic acid or ethyl acetate, respectively. Conversion is expressed as a percentage based on acetic acid or ethyl acetate in the feed. The conversion of acetic acid may be at least 40%, e.g., at least 50%, at least 60%, at least 70% or at least 80%. The conversion of ethyl acetate acid preferably is greater than 0%, meaning that more ethyl acetate is consumed than produced. During the hydrogenation of acetic acid, ethyl acetate may be produced. If the ethyl acetate produced is greater than the ethyl acetate consumed, the conversion of ethyl acetate would be negative. However, for purposes of the present invention, enough of the ethyl acetate is consumed to at least offset the produced ethyl acetate. Thus, preferably conversion of ethyl acetate may be at least 0%, e.g., at least 5%, at least 10%, at least 20%, or at least 35%. Although catalysts that have high conversions are desirable, especially acetic acid conversions that are at least 80% or at least 90%, in some embodiments a low acetic acid conversion may be acceptable at high selectivity for ethanol.

As indicated above, the present invention may determine when the ethyl acetate conversion is low or negative which indicates a decrease in catalyst activity. To maintain catalyst activity, water may be fed to the hydrogenation reactor. This advantageously promotes ethyl acetate conversion without impairing acetic acid conversion.

Selectivity is expressed as a mole percent based on converted acetic acid and/or ethyl acetate. It should be understood that each compound converted from acetic acid and/or ethyl acetate has an independent selectivity and that selectivity is independent from conversion. For example, if 60 mole % of the converted acetic acid is converted to ethanol, we refer to the ethanol selectivity as 60%. The total selectivity is based on the combined converted acetic acid and ethyl acetate. Preferably, the catalyst total selectivity to ethanol is at least 60%, e.g., at least 70%, or at least 80%. Preferably, the total selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. The productivity preferably may range from 100 to 3,000 grams of ethanol per kilogram of catalyst per hour.

In various embodiments of the present invention, the crude ethanol product produced by the reactor, before any subsequent processing, such as purification and separation, will typically comprise unreacted acetic acid, ethanol and water. Exemplary compositional ranges for the crude ethanol product are provided in Table 1. The "others" identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 72 | 15 to 72 | 15 to 70 | 25 to 65 |
| Acetic Acid | 0 to 90 | 0 to 50 | 0 to 35 | 0 to 15 |
| Water | 5 to 40 | 5 to 30 | 10 to 30 | 10 to 26 |
| Ethyl Acetate | 0 to 30 | 1 to 25 | 3 to 20 | 5 to 18 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product comprises acetic acid in an amount less than 20 wt. %, e.g., less than 15 wt. %, less than 10 wt. % or less than 5 wt. %. In terms of ranges, the acetic acid concentration of Table 1 may range from 0.1 wt. % to 20 wt. %, e.g., 0.2 wt. % to 15 wt. %, from 0.5 wt. % to 10 wt. % or from 1 wt. % to 5 wt. %. In embodiments having lower amounts of acetic acid, the conversion of acetic acid is preferably greater than 75%, e.g., greater than 85% or greater than 90%. In addition, the selectivity to ethanol may also be preferably high, and is preferably greater than 75%, e.g., greater than 85% or greater than 90%.

Depending on the crude ethanol product composition from the reactor, there may be several different processes for separating the impurities and recovering ethanol. Each separation and recovery processes uses a distillation column with an intermediate reboiler and a bottoms reboiler.

Figure 2:
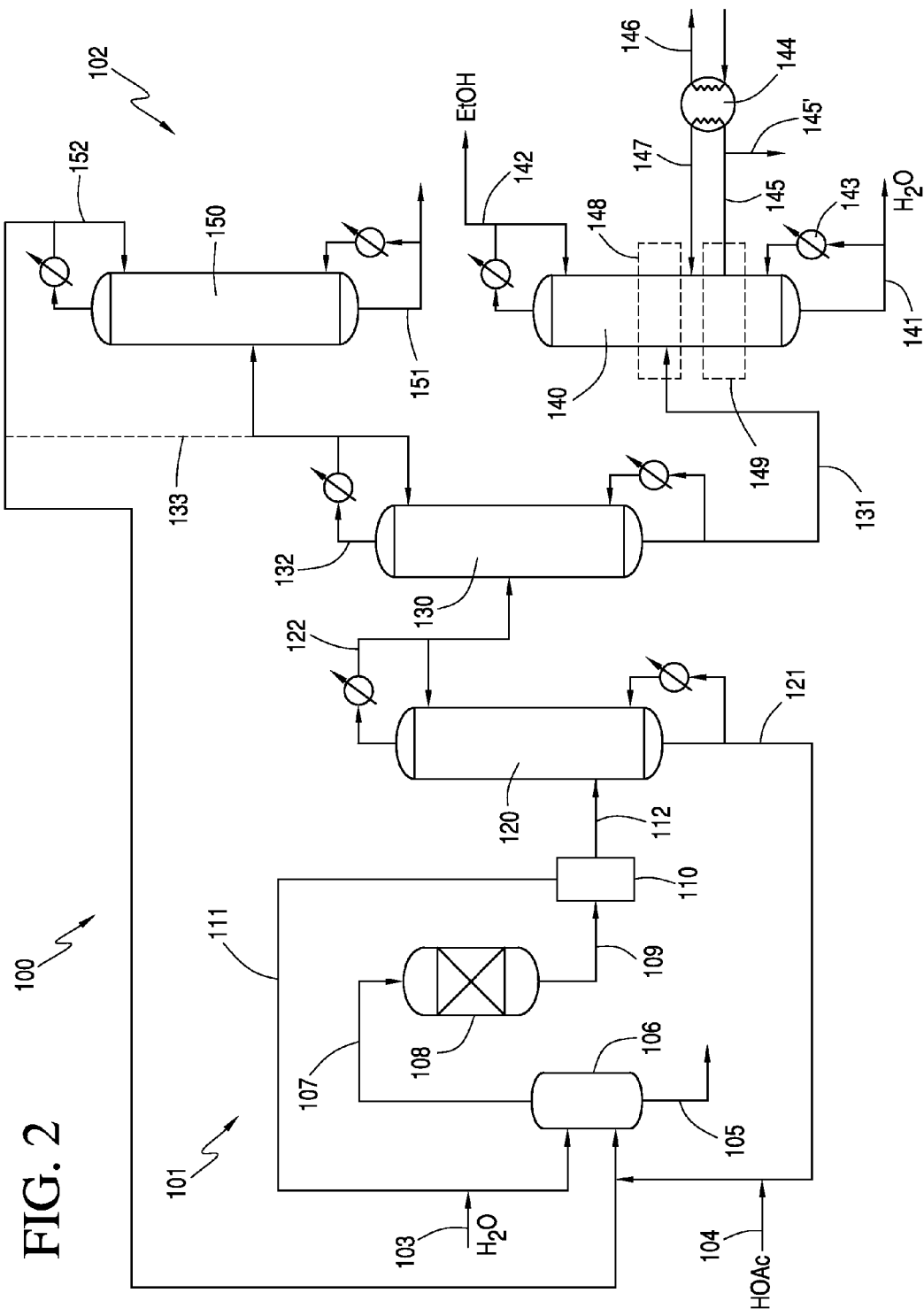
FIG. 2 is a schematic diagram of an ethanol production system with multiple distillation columns in accordance with one embodiment of the present invention.
Figure 3:
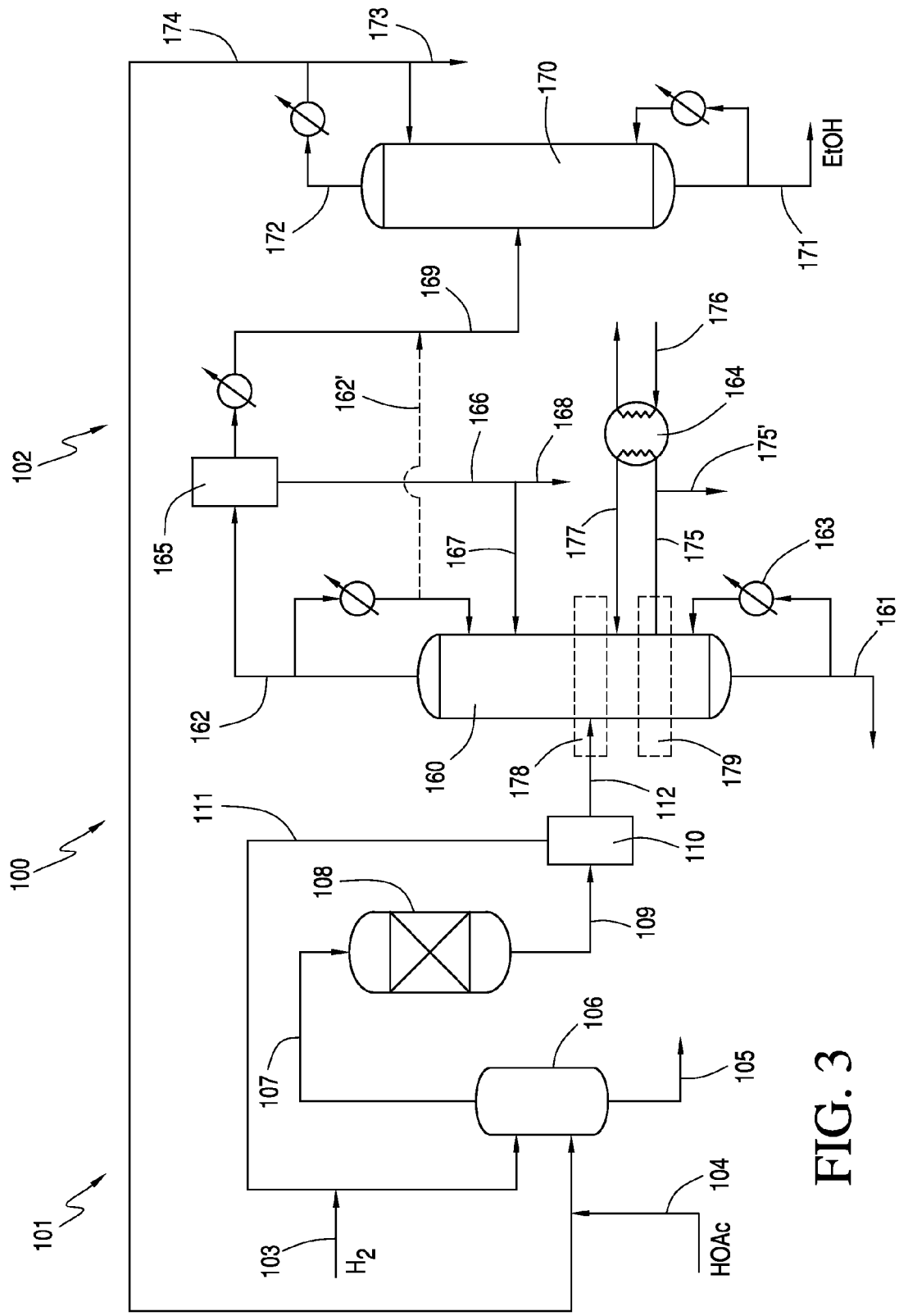
FIG. 3 is a schematic diagram of an ethanol production system with multiple distillation columns in accordance with another embodiment of the present invention.
Figure 4:
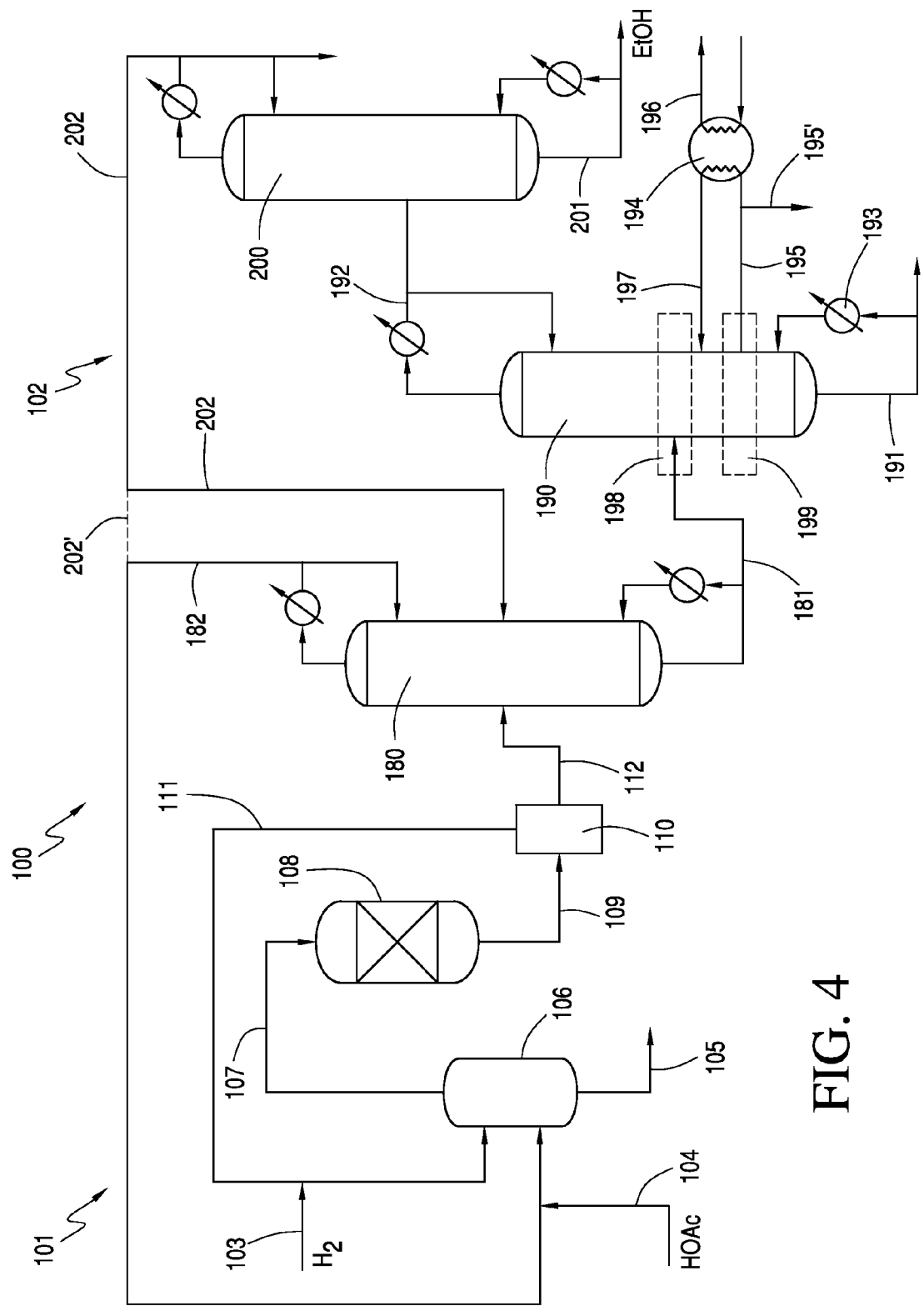
FIG. 4 is a schematic diagram of an ethanol production system with multiple distillation columns in accordance with one embodiment of the present invention.

FIGS. 2-4 illustrate various separation schemes for recovering ethanol, each of which use a distillation column with intermediate and bottoms reboilers as shown in FIG. 1. In FIG. 2, an acid stream and light ends stream are removed prior to separating the ethanol and water in a distillation column with intermediate and bottoms reboilers. In FIG. 3, the crude ethanol product or a liquid portion thereof is fed to a distillation column with intermediate and bottoms reboilers. Ethanol is subsequently further purified in additional columns. In FIG. 4, after separating a light ends stream, the remaining stream is fed to a distillation column with intermediate and bottoms reboilers. These separations are illustrative and the distillation column with intermediate and bottoms reboilers of the present invention may be used with further processes that separate ethanol and water.

In general, the hydrogenation system 100 in FIGS. 2-4 comprises reaction zone 101 and separation zone 102. Reaction zone comprises hydrogen in line 103 and a reactant feed in line 107 which are fed to a vaporizer 106 to create a vapor feed stream in line 107 that is directed to reactor 108. Hydrogen feed line 103 may be preheated to a temperature from 30° C. to 150° C., e.g., from 50° C. to 125° C. or from 60° C. to 115° C. Hydrogen feed line 103 may be fed at a pressure from 1300 kPa to 3100 kPa, e.g., from 1500 kPa to 2800 kPa, or 1700 kPa to 2600 kPa. Reactant in line 104 may comprise acetic acid and/or ethyl acetate. In one embodiment, reactant in line 104 comprises greater than 95 wt. % acetic acid. In another embodiment, reactant in line 104 comprises from 5 to 30 wt. % ethyl acetate and 70 to 95 wt. % acetic acid. The acetic acid and/or ethyl acetate may be recycled from within system 100 or is fresh. In one embodiment, lines 103 and 104 may be combined and jointly fed to vaporizer 106 to form a vapor feed stream in line 107. The temperature of vapor feed stream in line 109 is preferably from 100° C. to 350° C., e.g., from 120° C. to 310° C. or from 7150° C. to 300° C. Any feed that is not vaporized is removed from vaporizer 106 in blowdown stream 105 and may be recycled or discarded thereto. The mass ratio of vapor feed stream in line 109 to blowdown stream 110 may be from 6:1 to 500:1, e.g., from 10:1 to 500:1, from 20:1 to 500:1 or from 50:1 to 500:1. In addition, although vapor feed stream in line 107 is shown as being directed to the top of reactor 108, line 107 may be directed to the side, upper portion, or bottom.

In one embodiment, one or more guard beds (not shown) may be used upstream of the reactor, optionally upstream of vaporizer 106, to protect the catalyst from poisons or undesirable impurities contained in the feed or return/recycle streams. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens.

During the hydrogenation process, a crude ethanol product stream is withdrawn, preferably continuously, from reactor 108 via line 109.

The crude ethanol product stream in line 109 may be condensed and fed to a separator 110, which, in turn, provides a vapor stream 111 and a liquid stream 112. In some embodiments, separator 110 may comprise a flasher or a knockout pot. Separator 110 may operate at a temperature from 20° C. to 250° C., e.g., from 30° C. to 225° C. or from 60° C. to 200° C. The pressure of separator 110 may be from 50 kPa to 2000 kPa, e.g., from 75 kPa to 1500 kPa or from 100 kPa to 1000 kPa. Optionally, the crude ethanol product in line 109 may pass through one or more membranes to separate hydrogen and/or other non-condensable gases.

The vapor stream 111 exiting separator 110 may comprise hydrogen and hydrocarbons, and may be purged and/or returned to reaction zone 101. When returned to reaction zone 101, vapor stream 111 is combined with the hydrogen feed 103 and co-fed to vaporizer 106. In some embodiments, the returned vapor stream 111 may be compressed before being combined with hydrogen feed 103.

In FIG. 2, the liquid stream 112 from separator 110 is withdrawn and introduced in the lower part of first column 120, e.g., lower half or lower third. First column 120 is also referred to as an "acid separation column." In one embodiment, the contents of liquid stream 112 are substantially similar to the crude ethanol product obtained from the reactor, except that the composition has been depleted of hydrogen, carbon dioxide, methane and/or ethane, which are removed by separator 110. Accordingly, liquid stream 112 may also be referred to as a crude ethanol product. Exemplary components of liquid stream 112 are provided in Table 2. It should be understood that liquid stream 112 may contain other components, not listed in Table 2.

TABLE 2

COLUMN FEED COMPOSITION
(Liquid stream 112)

|  | Conc. (wt. %) | Conc. (wt. %) | Conc. (wt. %) |
|---|---|---|---|
| Ethanol | 5 to 72 | 10 to 70 | 15 to 65 |
| Acetic Acid | <90 | 0 to 50 | 0 to 35 |
| Water | 5 to 40 | 5 to 30 | 10 to 26 |
| Ethyl Acetate | <30 | 1 to 25 | 3 to 20 |
| Acetaldehyde | <10 | 0.001 to 3 | 0.1 to 3 |
| Acetals | <5 | 0.01 to 6 | 0.01 to 5 |
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The amounts indicated as less than (<) in the tables throughout the present specification may not be present and if present may be present in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 2 may include, but are not limited to, methanol, isopropanol, n-propanol, n-butanol, 2-butanol or mixtures thereof. In one embodiment, the liquid stream 112 may comprise propanol, e.g., isopropanol and/or n-propanol, in an amount from 0.001 to 0.1 wt. %, from 0.001 to 0.05 wt. % or from 0.001 to 0.03 wt. %. In should be understood that these other components may be carried through in any of the distillate or residue streams described herein and will not be further described herein, unless indicated otherwise.

Optionally, crude ethanol product in line 109 or in liquid stream 112 may be further fed to an esterification reactor, hydrogenolysis reactor, or combination thereof. An esterification reactor may be used to consume residual acetic acid present in the crude ethanol product to further reduce the amount of acetic acid that would otherwise need to be removed. Hydrogenolysis may be used to convert ethyl acetate in the crude ethanol product to ethanol.

In the embodiment shown in FIG. 2, line 112 is introduced in the lower part of first column 120, e.g., lower half or lower third. In first column 120, unreacted acetic acid, a portion of the water, and other heavy components, if present, are removed from the composition in line 121 and are withdrawn, preferably continuously, as residue. Some or all of the residue may be returned and/or recycled back to reaction zone 101 via line 121. Recycling the acetic acid in line 121 to the vaporizer 106 may reduce the amount of heavies that need to be purged from vaporizer 106. Optionally, at least a portion of residue in line 121 may be purged from the system. Reducing the amount of heavies to be purged may improve efficiencies of the process while reducing byproducts.

First column 120 also forms an overhead distillate, which is withdrawn in line 122, and which may be condensed and refluxed, for example, at a ratio from 10:1 to 1:10, e.g., from 3:1 to 1:3 or from 1:2 to 2:1.

When column 120 is operated under standard atmospheric pressure, the temperature of the residue exiting in line 121 preferably is from 95° C. to 120° C., e.g., from 110° C. to 117° C. or from 111° C. to 115° C. The temperature of the distillate exiting in line 122 preferably is from 70° C. to 110° C., e.g., from 75° C. to 95° C. or from 80° C. to 90° C. Column 120 preferably operates at ambient pressure. In other embodiments, the pressure of first column 120 may range from 0.1 kPa to 510 kPa, e.g., from 1 kPa to 475 kPa or from 1 kPa to 375 kPa. Exemplary components of the distillate and residue compositions for first column 120 are provided in Table 3 below. It should also be understood that the distillate and residue may also contain other components, not listed, such as components in the feed. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

ACID COLUMN 120 (FIG. 2)

|  | Conc. (wt. %) | Conc. (wt. %) | Conc. (wt. %) |
|---|---|---|---|
| Distillate |  |  |  |
| Ethanol | 20 to 75 | 30 to 70 | 40 to 65 |
| Water | 10 to 40 | 15 to 35 | 20 to 35 |
| Acetic Acid | <2 | 0.001 to 0.5 | 0.01 to 0.2 |
| Ethyl Acetate | <60 | 5.0 to 40 | 10 to 30 |
| Acetaldehyde | <10 | 0.001 to 5 | 0.01 to 4 |
| Acetals | 0.01 to 10 | 0.05 to 6 | 0.1 to 5 |
| Acetone | <0.05 | 0.001 to 0.03 | 0.01 to 0.025 |
| Residue |  |  |  |
| Acetic Acid | 60 to 100 | 70 to 95 | 85 to 92 |
| Water | <30 | 1 to 20 | 1 to 15 |
| Ethanol | <1 | <0.9 | <0.07 |

As shown in Table 3, without being bound by theory, it has surprisingly and unexpectedly been discovered that when any amount of acetal is detected in the feed that is introduced to the acid separation column 120, the acetal appears to decompose in the column such that less or even no detectable amounts are present in the distillate and/or residue.

The distillate in line 122 preferably comprises ethanol, ethyl acetate, and water, along with other impurities, which may be difficult to separate due to the formation of binary and tertiary azeotropes. To further separate distillate, line 122 is introduced to the second column 130, also referred to as the "light ends column," preferably in the middle part of column 123, e.g., middle half or middle third. Preferably the second column 130 is an extractive distillation column. In such embodiments, an extraction agent, such as water, may be added to second column 130. If the extraction agent comprises water, it may be obtained from an external source or from an internal return/recycle line from one or more of the other columns.

The molar ratio of the water in the extraction agent to the ethanol in the feed to the second column is preferably at least 0.5:1, e.g., at least 1:1 or at least 3:1. In terms of ranges, preferred molar ratios may range from 0.5:1 to 8:1, e.g., from 1:1 to 7:1 or from 2:1 to 6.5:1. Higher molar ratios may be used but with diminishing returns in terms of the additional ethyl acetate in the second distillate and decreased ethanol concentrations in the second column distillate.

In one embodiment, an additional extraction agent, such as water from an external source, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'-dimethyl-1,3-propanediamine, N,N'-dimethylethylenediamine, diethylene triamine, hexamethylene diamine and 1,3-diaminopentane, an alkylated thiopene, dodecane, tridecane, tetradecane and chlorinated paraffins, may be added to second column 130. Some suitable extraction agents include those described in U.S. Pat. Nos. 4,379,028, 4,569,726, 5,993,610 and 6,375,807, the entire contents and disclosure of which are hereby incorporated by reference.

In the embodiments of the present invention, without the use of an extractive agent, a larger portion of the ethanol would carry over into the second distillate in line 132. By using an extractive agent in second column 130, the separation of ethanol into the second residue in line 131 is facilitated thus increasing the yield of the overall ethanol product in the second residue in line 131.

Second column 130 may be a tray or packed column. In one embodiment, second column 130 is a tray column having from 5 to 70 trays, e.g., from 15 to 50 trays or from 20 to 45 trays. Although the temperature and pressure of second column 130 may vary, when at atmospheric pressure the temperature of the second residue exiting in line 131 preferably is from 60° C. to 90° C., e.g., from 70° C. to 90° C. or from 80° C. to 90° C. The temperature of the second distillate exiting in line 132 from second column 130 preferably is from 50° C. to 90° C., e.g., from 60° C. to 80° C. or from 60° C. to 70° C. Column 130 may operate at atmospheric pressure. In other embodiments, the pressure of second column 130 may range from 0.1 kPa to 510 kPa, e.g., from 1 kPa to 475 kPa or from 1 kPa to 375 kPa. Exemplary components for the distillate and residue compositions for second column 130 are provided in Table 4 below. It should be understood that the distillate and residue may also contain other components, not listed, such as components in the feed.

TABLE 4

| SECOND COLUMN 130 (FIG. 2) | | | |
|---|---|---|---|
|  | Conc. (wt. %) | Conc. (wt. %) | Conc. (wt. %) |
| Distillate | | | |
| Ethyl Acetate | 10 to 99 | 25 to 95 | 50 to 93 |
| Acetaldehyde | <25 | 0.5 to 15 | 1 to 8 |
| Water | <25 | 0.5 to 20 | 4 to 16 |
| Ethanol | <30 | 0.001 to 15 | 0.01 to 5 |
| Acetal | 0.01 to 20 | 1 to 20 | 5 to 20 |
| Residue | | | |
| Water | 30 to 90 | 40 to 85 | 50 to 85 |
| Ethanol | 10 to 75 | 15 to 60 | 20 to 50 |
| Ethyl Acetate | <3 | 0.001 to 2 | 0.001 to 0.5 |
| Acetic Acid | <0.5 | 0.001 to 0.3 | 0.01 0.2 |

In preferred embodiments, the recycling of the third residue promotes the separation of ethyl acetate from the residue of the second column 130. For example, the weight ratio of ethyl acetate in the second residue to second distillate preferably is less than 0.4:1, e.g., less than 0.2:1 or less than 0.1:1. In embodiments that use an extractive distillation column with water as an extraction agent as the second column 130, the weight ratio of ethyl acetate in the second residue to ethyl acetate in the second distillate approaches zero. Second residue may comprise, for example, from 30% to 99.5% of the water and from 85 to 100% of the acetic acid from line 122. The second distillate in line 132 comprises ethyl acetate and additionally comprises water, ethanol, and/or acetaldehyde.

The weight ratio of ethanol in the second residue to second distillate preferably is at least 3:1, e.g., at least 6:1, at least 8:1, at least 10:1 or at least 15:1. All or a portion of the third residue, discussed below, is recycled to the second column. In one embodiment, all of the third residue may be recycled until process 100 reaches a steady state and then a portion of the third residue is recycled with the remaining portion being purged from the system 100. The composition of the second residue will tend to have lower amounts of ethanol than when the third residue is not recycled. As the third residue is recycled, the composition of the second residue, as provided in Table 4, comprises less than 30 wt. % of ethanol, e.g., less than 20 wt. % or less than 15 wt. %. The majority of the second residue preferably comprises water. Notwithstanding this effect, the extractive distillation step advantageously also reduces the amount of ethyl acetate that is sent to the third column, which is highly beneficial in ultimately forming a highly pure ethanol product.

As shown, the second residue from second column 130, which comprises ethanol and water, is fed via line 131 to third column 140, also referred to as the "product column." In one embodiment, the second residue in line 131 may also be referred to as a dilute acid stream when it contains detectable amounts of acetic acid. More preferably, the second residue in line 131 is introduced in the lower part of third column 140, e.g., lower half or lower third. Third column 140 recovers ethanol, which preferably is substantially pure with respect to organic impurities and other than the azeotropic water content, as the distillate in line 142.

As shown in FIG. 2, the third residue, e.g. dilute acid stream, in line 131 is fed to third column 140. Third column 140 comprises inlet zone 148 and removal zone 149. Intermediate stream in line 145 is withdrawn from removal zone 149. Preferably, intermediate stream in line 145 comprises less ethanol, based on weight, than the third residue. At least a portion of intermediate stream may be purged via line 145'. The remainder of intermediate stream 145 is passed through intermediate reboiler 144 and returned to third column 140 via line 147. In some embodiments, intermediate stream in line 147 is returned to third column 140 above removal zone 149 but below inlet zone 148. Intermediate reboiler 144 is supplied with heat from a heating medium via lines 146. A residue is withdrawn from third column 140 via line 141 and is passed through a bottoms reboiler 143. The residue is then returned to third column 140 below removal zone 19.

The distillate of third column 140 preferably is refluxed as shown in FIG. 2, for example, at a reflux ratio from 1:10 to 10:1, e.g., from 1:3 to 3:1 or from 1:2 to 2:1. The third residue in line 141, which comprises primarily water, preferably is returned to the second column 130 as an extraction agent as described above. In one embodiment (not shown), a first portion of the third residue in line 141 is recycled to the second column and a second portion is purged and removed from the system. In one embodiment, once the process reaches steady state, the second portion of water to be purged is substantially similar to the amount water formed in the hydrogenation of acetic acid. In one embodiment, a portion of the third residue may be used to hydrolyze any other stream, such as one or more streams comprising ethyl acetate.

Third column 140 is preferably a tray column as described above and operates at atmospheric pressure or optionally at pressures above or below atmospheric pressure. The temperature of the third distillate exiting in line 142 preferably is from 50° C. to 110° C., e.g., from 70° C. to 100° C. or from 75° C. to 95° C. The temperature of the third residue in line 142 preferably is from 15° C. to 100° C., e.g., from 30° C. to 90° C. or from 50° C. to 80° C. Exemplary components of the distillate and residue compositions for third column 140 are provided in Table 5 below. It should be understood that the distillate and residue may also contain other components, not listed, such as components in the feed.

TABLE 5

| THIRD COLUMN 140 (FIG. 2) | | | |
|---|---|---|---|
|  | Conc. (wt. %) | Conc. (wt. %) | Conc. (wt. %) |
| Distillate | | | |
| Ethanol | 75 to 96 | 80 to 96 | 85 to 96 |
| Water | <12 | 1 to 9 | 3 to 8 |
| Acetic Acid | <12 | 0.0001 to 0.1 | 0.005 to 0.05 |
| Ethyl Acetate | <12 | 0.0001 to 0.05 | 0.005 to 0.025 |
| Acetaldehyde | <12 | 0.0001 to 0.1 | 0.005 to 0.05 |
| Acetal | <12 | 0.0001 to 0.05 | 0.005 to 0.01 |
| Residue | | | |
| Water | 75 to 99.9 | 80 to 99.9 | 90 to 99.5 |
| Ethanol | <0.8 | 0.001 to 0.5 | 0.005 to 0.05 |
| Ethyl Acetate | <1 | 0.001 to 0.5 | 0.005 to 0.2 |
| Acetic Acid | <2 | 0.001 to 0.5 | 0.005 to 0.2 |

In one embodiment, the third residue in line 141 is withdrawn from third column 140 at a temperature higher than the operating temperature of the second column 130.

Any of the compounds that are carried through the distillation process from the feed or crude reaction product generally remain in the third distillate in amounts of less 0.01 wt. %, based on the total weight of the third distillate composition, e.g., less than 0.05 wt. % or less than 0.02 wt. %. In one embodiment, one or more side streams may remove impurities from any of the columns in the system 100. Preferably at least one side stream is used to remove impurities from the third column 140. The impurities may be purged and/or retained within the system 100.

The third distillate in line 142 may be further purified to form an anhydrous ethanol product stream, i.e., "finished anhydrous ethanol," using one or more additional separation systems, such as, for example, distillation columns, adsorption units, membranes, or molecular sieves. Suitable adsorption units include pressure swing adsorption units and thermal swing adsorption unit.

Returning to second column 130, the second distillate preferably is refluxed as shown in FIG. 2, optionally at a reflux ratio of 1:10 to 10:1, e.g., from 1:5 to 5:1 or from 1:3 to 3:1. In one embodiment, at least a portion of second distillate in line 132 is further processed in fourth column 150, also referred to as the "acetaldehyde removal column." In fourth column 150, the second distillate is separated into a fourth distillate, which comprises acetaldehyde, in line 152 and a fourth residue, which comprises ethyl acetate, in line 151. The fourth distillate preferably is refluxed at a reflux ratio from 1:20 to 20:1, e.g., from 1:15 to 15:1 or from 1:10 to 10:1, and at least a portion of the fourth distillate is returned to vaporizer 106. Additionally, at least a portion of fourth distillate in line 152 may be purged. Without being bound by theory, since acetaldehyde may be reacted, e.g., by hydrogenation, to form ethanol, the recycling of a stream that contains acetaldehyde to the reaction zone increases the yield of ethanol and decreases byproduct and waste generation. In another embodiment, the acetaldehyde may be collected and utilized, with or without further purification, to make useful products including but not limited to n-butanol, 1,3-butanediol, and/or crotonaldehyde and derivatives.

The fourth residue of fourth column 150 may be purged via line 151. The fourth residue primarily comprises ethyl acetate and ethanol, which may be suitable for use as a solvent mixture or in the production of esters. In one preferred embodiment, the acetaldehyde is removed from the second distillate in fourth column 150 such that no detectable amount of acetaldehyde is present in the residue of column 150.

Fourth column 150 is a tray column as described above and may operate above atmospheric pressure. In one embodiment, the pressure is from 120 kPa to 5,000 kPa, e.g., from 200 kPa to 4,500 kPa, or from 400 kPa to 3,000 kPa. In a preferred embodiment the fourth column 150 may operate at a pressure that is higher than the pressure of the other columns.

The temperature of the fourth distillate exiting in line 152 preferably is from 60° C. to 110° C., e.g., from 70° C. to 100° C. or from 75° C. to 95° C. The temperature of the residue in line 151 preferably is from 70° C. to 115° C., e.g., from 80° C. to 110° C. or from 85° C. to 110° C. Exemplary components of the distillate and residue compositions for fourth column 150 are provided in Table 6 below. It should be understood that the distillate and residue may also contain other components, not listed, such as components in the feed.

TABLE 6

| FOURTH COLUMN 150 (FIG. 2) | | | |
|---|---|---|---|
| | Conc. (wt. %) | Conc. (wt. %) | Conc. (wt. %) |
| Distillate | | | |
| Ethyl Acetate | 2 to 80 | 2 to 50 | 5 to 40 |
| Acetaldehyde | <90 | 30 to 80 | 40 to 75 |
| Ethanol | <30 | 0.001 to 25 | 0.01 to 20 |
| Water | <25 | 0.001 to 20 | 0.01 to 15 |
| Residue | | | |
| Ethyl Acetate | 40 to 100 | 50 to 100 | 60 to 100 |
| Ethanol | <40 | 0.001 to 30 | 0.01 to 15 |

TABLE 6-continued

| FOURTH COLUMN 150 (FIG. 2) | | | |
|---|---|---|---|
| | Conc. (wt. %) | Conc. (wt. %) | Conc. (wt. %) |
| Water | <25 | 0.001 to 20 | 2 to 15 |
| Acetaldehyde | <1 | 0.001 to 0.5 | Not detectable |
| Acetal | <3 | 0.0001 to 2 | 0.01 0.01 |

In one embodiment, a portion of the third residue in line 141 is recycled to second column 130. In one embodiment, recycling the third residue further reduces the aldehyde components in the second residue and concentrates these aldehyde components in second distillate in line 132 and thereby sent to fourth column 150, wherein the aldehydes may be more easily separated. The third distillate in line 142 may have lower concentrations of aldehydes and esters due to the recycling of third residue in line 141.

FIG. 3 illustrates another exemplary separation system. The reaction zone 101 of FIG. 3 is similar to FIG. 2 and produces a liquid stream 112, e.g., crude ethanol product, for further separation. In one preferred embodiment, the reaction zone 101 of FIG. 3, in particular reactor 108, operates at above 80% acetic acid conversion, e.g., above 90% conversion or above 99% conversion. Thus, the acetic acid concentration in the liquid stream 112 may be low.

Liquid stream 112, also referred to as a dilute acid stream, is introduced in the middle or lower portion of a first column 160, also referred to as acid-water column. For purposes of convenience, the columns in each exemplary separation process, may be referred as the first, second, third, etc., columns, but it is understood that first column 160 in FIG. 3 operates differently than the first column 120 of FIG. 2. In one embodiment, no entrainers are added to first column 160.

As shown in FIG. 3, a dilute acid stream in line 112 is fed to first column 160. First column 160 comprises inlet zone 178 and removal zone 179. Intermediate stream in line 175 is withdrawn from removal zone 179. At least a portion of intermediate stream may be purged via line 175'. The remainder of intermediate stream 175 is passed through intermediate reboiler 164 and returned to first column 160 via line 177. In some embodiments, intermediate stream in line 177 is returned to first column 160 above removal zone 179 but below inlet zone 178. Intermediate reboiler 174 is supplied with heat from a heating medium via lines 176. A residue, comprising water, unreacted acetic acid, and any other heavy components (if present), is withdrawn from distillation column 160 via line 161 and is passed through a bottoms reboiler 163. The residue is then returned to second column 160 below removal zone 179. Preferably, a substantial portion of the water in the crude ethanol product that is fed to first column 160 may be removed in the first residue, for example, up to about 75% or to about 90% of the water from the crude ethanol product. First column 160 also forms a first distillate, which is withdrawn in line 162.

When column 160 is operated under about 170 kPa, the temperature of the residue exiting in line 161 preferably is from 90° C. to 130° C., e.g., from 95° C. to 120° C. or from 100° C. to 115° C. The temperature of the distillate exiting in line 162 preferably is from 60° C. to 90° C., e.g., from 65° C. to 85° C. or from 70° C. to 80° C. In some embodiments, the pressure of first column 160 may range from 0.1 kPa to 510 kPa, e.g., from 1 kPa to 475 kPa or from 1 kPa to 375 kPa.

The first distillate in line 162 comprises water, in addition to ethanol and other organics. In terms of ranges, the concentration of water in the first distillate in line 162 preferably is less than 20 wt. %, e.g., from 1 wt. % to 19 wt. % or from 5 wt.

% to 15 wt. %. A portion of first distillate in line 162 may be condensed and refluxed, for example, at a ratio from 10:1 to 1:10, e.g., from 3:1 to 1:3 or from 1:2 to 2:1. It is understood that reflux ratios may vary with the number of stages, feed locations, column efficiency and/or feed composition. Operating with a reflux ratio of greater than 3:1 may be less preferred because more energy may be required to operate the first column 160. The condensed portion of the first distillate may also be fed to a second column 170.

The remaining portion of the first distillate in 162 is fed to a water separation unit 165. Water separation unit 165 may be an adsorption unit, membrane, molecular sieves, extractive column distillation, or a combination thereof. A membrane or an array of membranes may also be employed to separate water from the distillate. The membrane or array of membranes may be selected from any suitable membrane that is capable of removing a permeate water stream from a stream that also comprises ethanol and ethyl acetate.

In a preferred embodiment, water separator 165 is a pressure swing adsorption (PSA) unit. The PSA unit is optionally operated at a temperature from 30° C. to 160° C., e.g., from 80° C. to 140° C., and a pressure from 0.01 kPa to 550 kPa, e.g., from 1 kPa to 150 kPa. The PSA unit may comprise two to five beds. Water separator 165 may remove at least 95% of the water from the portion of first distillate in line 162, and more preferably from 99% to 99.99% of the water from the first distillate, in a water stream 166. All or a portion of water stream 166 may be returned to column 160 in line 167, where the water preferably is ultimately recovered from column 160 in the first residue in line 161. Additionally or alternatively, all or a portion of water stream 166 may be purged via line 168. The remaining portion of first distillate exits the water separator 165 as ethanol mixture stream 169. Ethanol mixture stream 169 may have a low concentration of water of less than 10 wt. %, e.g., less than 6 wt. % or less than 2 wt. %. Exemplary components of ethanol mixture stream 169 and first residue in line 161 are provided in Table 7 below. It should also be understood that these streams may also contain other components, not listed, such as components derived from the feed.

TABLE 7

FIRST COLUMN 160 WITH PSA (FIG. 3)

|  | Conc. (wt. %) | Conc. (wt. %) | Conc. (wt. %) |
|---|---|---|---|
| Ethanol Mixture Stream |  |  |  |
| Ethanol | 20 to 95 | 30 to 95 | 40 to 95 |
| Water | <10 | 0.01 to 6 | 0.1 to 2 |
| Acetic Acid | <2 | 0.001 to 0.5 | 0.01 to 0.2 |
| Ethyl Acetate | <60 | 1 to 55 | 5 to 55 |
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| Residue |  |  |  |
| Acetic Acid | <90 | 1 to 50 | 2 to 35 |
| Water | 30 to 100 | 45 to 95 | 60 to 90 |
| Ethanol | <1 | <0.9 | <0.3 |

Preferably, ethanol mixture stream 169 is not returned or refluxed to first column 160. The condensed portion of the first distillate in line 162' may optionally be combined with ethanol mixture stream 169 to control the water concentration fed to the second column 170. For example, in some embodiments the first distillate may be split into equal portions, while in other embodiments, all of the first distillate may be condensed or all of the first distillate may be processed in the water separation unit. In FIG. 3, the condensed portion in line 162' and ethanol mixture stream 169 are co-fed to second column 170. In other embodiments, the condensed portion in line 162' and ethanol mixture stream 169 may be separately fed to second column 170. The combined distillate and ethanol mixture has a total water concentration of greater than 0.5 wt. %, e.g., greater than 2 wt. % or greater than 5 wt. %. In terms of ranges, the total water concentration of the combined distillate and ethanol mixture may be from 0.5 to 15 wt. %, e.g., from 2 to 12 wt. %, or from 5 to 10 wt. %.

The second column 170 in FIG. 3, also referred to as the "light ends column," removes ethyl acetate and acetaldehyde from the first distillate in line 172 and/or ethanol mixture stream 169. Ethyl acetate and acetaldehyde are removed as a second distillate in line 172 and ethanol is removed as the second residue in line 171. Second column 170 may be a tray column or packed column. In one embodiment, second column 170 is a tray column having from 5 to 70 trays, e.g., from 15 to 50 trays or from 20 to 45 trays.

Second column 170 operates at a pressure ranging from 0.1 kPa to 510 kPa, e.g., from 10 kPa to 450 kPa or from 50 kPa to 350 kPa. Although the temperature of second column 170 may vary, when at about 20 kPa to 70 kPa, the temperature of the second residue exiting in line 171 preferably is from 30° C. to 75° C., e.g., from 35° C. to 70° C. or from 40° C. to 65° C. The temperature of the second distillate exiting in line 172 preferably is from 20° C. to 55° C., e.g., from 25° C. to 50° C. or from 30° C. to 45° C.

The total concentration of water fed to second column 170 preferably is less than 10 wt. %, as discussed above. When first distillate in line 162 and/or ethanol mixture stream comprises minor amounts of water, e.g., less than 1 wt. % or less than 0.5 wt. %, additional water may be fed to the second column 170 as an extractive agent in the upper portion of the column. A sufficient amount of water is preferably added via the extractive agent such that the total concentration of water fed to second column 170 is from 1 to 10 wt. % water, e.g., from 2 to 6 wt. %, based on the total weight of all components fed to second column 170. If the extractive agent comprises water, the water may be obtained from an external source or from an internal return/recycle line from one or more of the other columns or water separators.

Suitable extractive agents may also include, for example, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'-dimethyl-1,3-propanediamine, N,N'-dimethylethylenediamine, diethylene triamine, hexamethylene diamine and 1,3-diaminopentane, an alkylated thiopene, dodecane, tridecane, tetradecane, chlorinated paraffins, or a combination thereof. When extractive agents are used, a suitable recovery system, such as a further distillation column, may be used to recycle the extractive agent.

Exemplary components for the second distillate and second residue compositions for the second column 170 are provided in Table 8, below. It should be understood that the distillate and residue may also contain other components, not listed in Table 8.

TABLE 8

SECOND COLUMN 170 (FIG. 3)

|  | Conc. (wt. %) | Conc. (wt. %) | Conc. (wt. %) |
|---|---|---|---|
| Second Distillate |  |  |  |
| Ethyl Acetate | 5 to 90 | 10 to 80 | 15 to 75 |
| Acetaldehyde | <60 | 1 to 40 | 1 to 35 |
| Ethanol | <45 | 0.001 to 40 | 0.01 to 35 |
| Water | <20 | 0.01 to 10 | 0.1 to 5 |
| Second Residue |  |  |  |
| Ethanol | 80 to 99.5 | 85 to 97 | 90 to 95 |
| Water | <20 | 0.001 to 15 | 0.01 to 10 |
| Ethyl Acetate | <1 | 0.001 to 2 | 0.001 to 0.5 |
| Acetic Acid | <0.5 | <0.01 | 0.001 to 0.01 |
| Acetal | <0.05 | <0.03 | <0.01 |

TABLE 9

FIRST COLUMN 180 (FIG. 4)

|  | Conc. (wt. %) | Conc. (wt. %) | Conc. (wt. %) |
|---|---|---|---|
| Distillate |  |  |  |
| Ethyl Acetate | 10 to 85 | 15 to 80 | 20 to 75 |
| Acetaldehyde | 0.1 to 70 | 0.2 to 65 | 0.5 to 65 |
| Diethyl Acetal | 0.01 to 10 | 0.01 to 6 | 0.01 to 5 |
| Acetone | <0.05 | 0.001 to 0.03 | 0.01 to 0.025 |
| Ethanol | 3 to 55 | 4 to 50 | 5 to 45 |
| Water | 0.1 to 20 | 1 to 15 | 2 to 10 |
| Acetic Acid | <2 | <0.1 | <0.05 |
| Residue |  |  |  |
| Acetic Acid | 0.01 to 35 | 0.1 to 30 | 0.2 to 25 |
| Water | 5 to 40 | 10 to 35 | 15 to 30 |
| Ethanol | 10 to 75 | 15 to 70 | 20 to 65 |

The second residue in FIG. 3 comprises one or more impurities selected from the group consisting of ethyl acetate, acetic acid, and acetaldehyde. The second residue may comprise at least 100 wppm of these impurities, e.g., at least 250 wppm or at least 500 wppm. In some embodiments, the second residue may contain substantially no ethyl acetate or acetaldehyde.

The second distillate in line 171, which comprises ethyl acetate and/or acetaldehyde, preferably is refluxed as shown in FIG. 3, for example, at a reflux ratio from 1:30 to 30:1, e.g., from 1:10 to 10:1 or from 1:3 to 3:1. Additionally, at least a portion of second distillate 171 may be purged.

FIG. 4 illustrates another exemplary separation system. The reaction zone 101 of FIG. 4 is similar to FIG. 2 and produces a liquid stream 112, e.g., crude ethanol product, for further separation. In one preferred embodiment, the reaction zone 101 of FIG. 4, in particular reactor 108, operates at above 80% acetic acid conversion, e.g., above 90% conversion or above 99% conversion. Thus, the acetic acid concentration in the liquid stream 112 may be low.

In the exemplary embodiment shown in FIG. 4, liquid stream 112 is introduced in the lower part of first column 180, e.g., lower half or middle third. In one embodiment, no entrainers are added to first column 180. In first column 180, a weight majority of the ethanol, water, acetic acid, and other heavy components, if present, are removed from liquid stream 112 and are withdrawn, preferably continuously, as residue in line 181. First column 180 also forms an overhead distillate, which is withdrawn in line 182, and which may be condensed and refluxed, for example, at a ratio from 30:1 to 1:30, e.g., from 10:1 to 1:10 or from 1:5 to 5:1. The overhead distillate in stream 182 preferably comprises a weight majority of the ethyl acetate from liquid stream 112.

When column 180 is operated under about 170 kPa, the temperature of the residue exiting in line 181 preferably is from 70° C. to 155° C., e.g., from 90° C. to 130° C. or from 100° C. to 110° C. The base of column 180 may be maintained at a relatively low temperature by withdrawing a residue stream comprising ethanol, water, and acetic acid, thereby providing an energy efficiency advantage. The temperature of the distillate exiting in line 182 from column 180 preferably at 170 kPa is from 75° C. to 100° C., e.g., from 75° C. to 83° C. or from 81° C. to 84° C. In some embodiments, the pressure of first column 180 may range from 0.1 kPa to 510 kPa, e.g., from 1 kPa to 475 kPa or from 1 kPa to 375 kPa. Exemplary components of the distillate and residue compositions for first column 180 are provided in Table 9 below. It should also be understood that the distillate and residue may also contain other components, not listed in Table 9.

In one embodiment of the present invention, column 180 may be operated at a temperature where most of the water, ethanol, and acetic acid are removed from the residue stream and only a small amount of ethanol and water is collected in the distillate stream due to the formation of binary and tertiary azeotropes. The weight ratio of water in the residue in line 181 to water in the distillate in line 182 may be greater than 1:1, e.g., greater than 2:1. The weight ratio of ethanol in the residue to ethanol in the distillate may be greater than 1:1, e.g., greater than 2:1

The amount of acetic acid in the first residue may vary depending primarily on the conversion in reactor 108. In one embodiment, when the conversion is high, e.g., greater than 90%, the amount of acetic acid in the first residue may be less than 10 wt. %, e.g., less than 5 wt. % or less than 2 wt. %. In other embodiments, when the conversion is lower, e.g., less than 90%, the amount of acetic acid in the first residue may be greater than 10 wt. %.

The distillate preferably is substantially free of acetic acid, e.g., comprising less than 1000 wppm, less than 500 wppm or less than 100 wppm acetic acid. The distillate may be purged from the system or recycled in whole or part to reactor 108. In some embodiments, the distillate may be further separated, e.g., in a distillation column (not shown), into an acetaldehyde stream and an ethyl acetate stream. Either of these streams may be returned to the reactor 108 or separated from system 100 as a separate product.

Some species, such as acetals, may decompose in first column 180 such that very low amounts, or even no detectable amounts, of acetals remain in the distillate or residue.

To recover ethanol, the residue in line 181 may be further separated in a second column 190, also referred to as an "acid separation column." An acid separation column may be used when the acetic acid concentration in the first residue is greater than 1 wt. %, e.g., greater than 5 wt. %. The first residue in line 181, also referred to as a dilute acid stream, is introduced to second column 190 preferably in the top part of column 190, e.g., top half or top third. Second column 190 comprises inlet zone 198 and removal zone 199. Intermediate stream in line 195 is withdrawn from removal zone 199. Intermediate stream may contain more acetic acid, based on weight, than first residue. At least a portion of intermediate stream may be purged via line 195'. The remainder of intermediate stream 195 is passed through intermediate reboiler 194 and returned to second column 190 via line 197. In some embodiments, intermediate stream in line 197 is returned to second column 190 above removal zone 199 but below inlet zone 198. Intermediate reboiler 194 is supplied with heat from a heating medium via lines 196. A residue, comprising water and acetic acid, is withdrawn from distillation column 190 via line 191 and is passed through a bottoms reboiler 193. The residue is then returned to second column 190 below removal zone 199.

Second column 190 also yields a second distillate in line 192 comprising ethanol. Second column 190 may be a tray column or packed column. In one embodiment, second column 190 is a tray column having from 5 to 150 trays, e.g., from 15 to 50 trays or from 20 to 45 trays. Although the temperature and pressure of second column 190 may vary, when at atmospheric pressure the temperature of the second residue exiting in line 191 preferably is from 95° C. to 130° C., e.g., from 100° C. to 125° C. or from 110° C. to 120° C. The temperature of the second distillate exiting in line 192 preferably is from 60° C. to 100° C., e.g., from 75° C. to 100° C. or from 80° C. to 100° C. The pressure of second column 190 may range from 0.1 kPa to 510 kPa, e.g., from 1 kPa to 475 kPa or from 1 kPa to 375 kPa. Exemplary components for the distillate and residue compositions for second column 190 are provided in Table 10 below. It should be understood that the distillate and residue may also contain other components, not listed in Table 10.

TABLE 10

SECOND COLUMN 190 (FIG. 4)

|  | Conc. (wt. %) | Conc. (wt. %) | Conc. (wt. %) |
|---|---|---|---|
| Second Distillate | | | |
| Ethanol | 70 to 99.9 | 75 to 98 | 80 to 95 |
| Ethyl Acetate | <10 | 0.001 to 5 | 0.01 to 3 |
| Acetaldehyde | <5 | 0.001 to 1 | 0.005 to 0.5 |
| Acetal | 0.01 to 10 | 0.01 to 6 | 0.01 to 5 |
| Water | 0.1 to 30 | 1 to 25 | 5 to 20 |
| Second Residue | | | |
| Acetic Acid | 0.1 to 45 | 0.2 to 40 | 0.5 to 35 |
| Water | 45 to 100 | 55 to 99.8 | 65 to 99.5 |
| Ethyl Acetate | <2 | <1 | <0.5 |
| Ethanol | <5 | 0.015 | <2 |

The weight ratio of ethanol in the second distillate in line 192 to ethanol in the second residue in line 191 preferably is at least 35:1. In one embodiment, the weight ratio of water in the second residue 191 to water in the second distillate 192 is greater than 2:1, e.g., greater than 4:1 or greater than 6:1. In addition, the weight ratio of acetic acid in the second residue 191 to acetic acid in the second distillate 192 preferably is greater than 10:1, e.g., greater than 15:1 or greater than 20:1. Preferably, the second distillate in line 192 is substantially free of acetic acid and may only contain, if any, trace amounts of acetic acid.

As shown, the second distillate in line 190 is fed to a third column 200, e.g., ethanol product column, for separating the second distillate into a third distillate (ethyl acetate distillate) in line 202 and a third residue (ethanol residue) in line 201. Second distillate in line 192 may be introduced into the lower part of column 200, e.g., lower half or lower third. Third distillate 202 is preferably refluxed, for example, at a reflux ratio greater than 2:1, e.g., greater than 5:1 or greater than 10:1. Additionally, at least a portion of third distillate 202 may be purged. Third column 200 is preferably a tray column as described herein and preferably operates at atmospheric pressure. The temperature of the third residue exiting from third column 201 preferably is from 60° C. to 110° C., e.g., from 70° C. to 100° C. or from 75° C. to 95° C. The temperature of the third distillate exiting from third column 200 preferably is from 70° C. to 115° C., e.g., from 80° C. to 110° C. or from 85° C. to 105° C., when the column is operated at atmospheric pressure.

In one embodiment, third distillate in line 202 may be introduced into first column 180.

The remaining water from the second distillate in line 192 may be removed in further embodiments of the present invention. Depending on the water concentration, the ethanol product may be derived from the second distillate in line 192 or the third residue in line 201. Some applications, such as industrial ethanol applications, may tolerate water in the ethanol product, while other applications, such as fuel applications, may require an anhydrous ethanol. The amount of water in the distillate of line 192 or the residue of line 201 may be closer to the azeotropic amount of water, e.g., at least 4 wt. %, preferably less than 20 wt. %, e.g., less than 12 wt. % or less than 7.5 wt. %. Water may be removed from the second distillate in line 192 or the third residue in line 201 using several different separation techniques as described herein. Particularly preferred techniques include the use of distillation column, membranes, adsorption units, and combinations thereof.

Some of the residues withdrawn from the separation zone 102 comprise acetic acid and water. Depending on the amount of water and acetic acid contained in the residue of first column, e.g., 120 in FIG. 2, 160 in FIG. 3, or residue of second column 190 in FIG. 4, the residue may be treated in one or more of the following processes. The following are exemplary processes for further treating the residue and it should be understood that any of the following may be used regardless of acetic acid concentration. When the residue comprises a majority of acetic acid, e.g., greater than 70 wt. %, the residue may be recycled to the reactor without any separation of the water. In one embodiment, the residue may be separated into an acetic acid stream and a water stream when the residue comprises a majority of acetic acid, e.g., greater than 50 wt. %. Acetic acid may also be recovered in some embodiments from the residue having a lower acetic acid concentration. The residue may be separated into the acetic acid and water streams by a distillation column or one or more membranes. If a membrane or an array of membranes is employed to separate the acetic acid from the water, the membrane or array of membranes may be selected from any suitable acid resistant membrane that is capable of removing a permeate water stream. The resulting acetic acid stream optionally is returned to the reactor 108. The resulting water stream may be used as an extractive agent or to hydrolyze an ester-containing stream in a hydrolysis unit.

In other embodiments, for example, where the residue comprises less than 50 wt. % acetic acid, possible options include one or more of: (i) returning a portion of the residue to reactor 108, (ii) neutralizing the acetic acid, (iii) reacting the acetic acid with an alcohol, or (iv) disposing of the residue in a waste water treatment facility. It also may be possible to separate a residue comprising less than 50 wt. % acetic acid using a weak acid recovery distillation column to which a solvent (optionally acting as an azeotroping agent) may be added. Exemplary solvents that may be suitable for this purpose include ethyl acetate, propyl acetate, isopropyl acetate, butyl acetate, vinyl acetate, diisopropyl ether, carbon disulfide, tetrahydrofuran, isopropanol, ethanol, and $C_3$-$C_{12}$ alkanes. When neutralizing the acetic acid, it is preferred that the residue comprises less than 10 wt. % acetic acid. Acetic acid may be neutralized with any suitable alkali or alkaline earth metal base, such as sodium hydroxide or potassium hydroxide. When reacting acetic acid with an alcohol, it is preferred that the residue comprises less than 50 wt. % acetic acid. The alcohol may be any suitable alcohol, such as methanol, ethanol, propanol, butanol, or mixtures thereof. The reaction forms an ester that may be integrated with other systems, such as carbonylation production or an ester production process. Preferably, the alcohol comprises ethanol and the resulting ester comprises ethyl acetate. Optionally, the resulting ester may be fed to the hydrogenation reactor.

In some embodiments, when the residue comprises very minor amounts of acetic acid, e.g., less than 5 wt. % or less than 1 wt. %, the residue may be neutralized and/or diluted before being disposed of to a waste water treatment facility. The organic content, e.g., acetic acid content, of the residue beneficially may be suitable to feed microorganisms used in a waste water treatment facility.

In some embodiments the desired ethanol product is an anhydrous ethanol that is suitable for uses as a fuel or as a blend for other fuels, such as gasoline. Water separation unit as described herein may be suitable for producing anhydrous ethanol.

The columns shown in FIGS. 1 to 4 may comprise any distillation column capable of performing the desired separation and/or purification. Each column comprises a tray column having from 1 to 150 trays, e.g., from 10 to 100 trays, from 20 to 95 trays or from 30 to 75 trays. In some embodiments, when the combined column has at least 70 trays, the intermediate stream may be returned between trays 20 and 50. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in one or more columns, preferably two or more columns such that the vapor from the first section enters the second section while the liquid from the second section enters the first section, etc.

The associated condensers and liquid separation vessels that may be employed with each of the distillation columns may be of any conventional design and are simplified in the figures. Heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in the figures, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. As a practical matter, pressures from 10 kPa to 3000 kPa will generally be employed in these zones although in some embodiments subatmospheric pressures or superatmospheric pressures may be employed. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

The ethanol product produced by the process of the present invention may be an industrial grade ethanol comprising from 75 to 99.5 wt. % ethanol, e.g., from 80 to 96 wt. % or from 85 to 96 wt. % ethanol, based on the total weight of the ethanol product. Exemplary finished ethanol compositional ranges are provided below in Table 11.

TABLE 11

FINISHED ETHANOL COMPOSITIONS

| Component | Conc. (wt. %) | Conc. (wt. %) | Conc. (wt. %) |
|---|---|---|---|
| Ethanol | 75 to 96 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

In some embodiments, when further water separation is used, the ethanol product may be withdrawn as a stream from the water separation unit as discussed above. In such embodiments, the ethanol concentration of the ethanol product may be higher than indicated in Table 12, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including applications as fuels, solvents, chemical feedstocks, pharmaceutical products, cleansers, sanitizers, hydrogen transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entireties of which is incorporated herein by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

I claim:

1. A process for refining ethanol from a dilute acid stream, comprising:
    introducing the dilute acid stream to an inlet zone of a distillation column to yield an overhead comprising ethanol; wherein the dilute acid stream comprises from 0.1 to 10 wt. % acid;
    recirculating an intermediate stream, withdrawn from a removal zone, by passing the intermediate stream through an intermediate reboiler and returning the intermediate stream to the distillation column at or adjacent to the removal zone to supply heat to the distillation column,
    heating the distillation column below the removal zone with a bottoms reboiler and withdrawing a residue therefrom, wherein the residue comprises water and substantially all of the acid from the dilute acid stream; and
    recovering an ethanol product from the overhead;
    wherein the intermediate reboiler is operated under non-esterification conditions, wherein less than 1000 ppm of ethyl acetate is formed in the intermediate reboiler.

2. The process of claim 1, wherein the removal zone is below the inlet zone.

3. The process of claim 1, wherein the removal zone is operated at a temperature above 80° C.

4. The process of claim 1, wherein the intermediate stream is returned above the removal zone.

5. The process of claim 1, wherein the intermediate stream is returned above the inlet zone.

6. The process of claim 1, wherein the intermediate reboiler is selected from the group consisting of internal reboiler, kettle reboiler, jacketed kettle reboiler, thermosyphon reboiler, falling film reboiler, fire reboiler, and forced circulation reboiler.

7. The process of claim 1, wherein the intermediate reboiler supplies from 5 to 60% of total heat to the distillation column.

8. The process of claim 1, wherein the ethanol product comprises from 1 to 100 wppm acid.

9. The process of claim 1, wherein the dilute acid stream comprises from 0.5 wt. % to 5 wt. % acid.

10. The process of claim 1, wherein the dilute acid stream is substantially free of methanol.

11. A process for refining ethanol, comprising:
    hydrogenating acetic acid and/or an ester thereof in a reactor in the presence of a catalyst to form a crude ethanol product;
    obtaining a dilute acid stream from the crude ethanol product that comprises a portion of the ethanol from the crude ethanol product;
    introducing the dilute acid stream to an inlet zone of a distillation column to yield an overhead comprising ethanol, wherein the dilute acid stream comprises from 0.01 to 10 wt. % acid;
    recirculating an intermediate stream, withdrawn from a removal zone, by passing the intermediate stream through an intermediate reboiler and returning the intermediate stream to the distillation column at or adjacent to the removal zone to supply heat to the distillation column,
    heating the distillation column below the removal zone with a bottoms reboiler and withdrawing a residue therefrom; and
    recovering an ethanol product from the overhead;
    wherein the intermediate reboiler is operated under non-esterification conditions, wherein less than 1000 ppm of ethyl acetate is formed in the intermediate reboiler.

12. The process of claim 11, wherein the residue comprises water and all of the acetic acid from the dilute acid stream.

13. The process of claim 11, wherein the removal zone is operated at a temperature above 80° C.

14. The process of claim 11, wherein the boiling point of the intermediate stream is at least 5% lower than the boiling point of the residue.

15. The process of claim 11, wherein the intermediate reboiler supplies from 5 to 60% of total heat to the distillation column.

16. The process of claim 11, wherein the ethanol product comprises from 1 to 100 wppm acetic acid.

17. A process for refining ethanol from a dilute acid stream, comprising:
    hydrogenating acetic acid and/or an ester thereof in a reactor in the presence of a catalyst to form a crude ethanol product;
    separating at least a portion of the crude ethanol product in a first distillation column to yield a first distillate comprising ethanol, ethyl acetate and water and a first residue comprising acetic acid;
    separating at least a portion of the first distillate in a second distillation column to yield a second distillate comprising ethyl acetate and a second residue comprising from 0.1 to 10 wt. % acetic acid, ethanol and water;
    separating at least a portion of the second residue in a third distillation column by introducing the second residue to an inlet zone of the third distillation column to yield an overhead comprising ethanol;
    recirculating an intermediate stream, withdrawn from a removal zone, by passing the intermediate stream through an intermediate reboiler and returning the intermediate stream to the third distillation column at or adjacent to the removal zone to supply heat to the third distillation column;
    heating the distillation column below the removal zone with a bottoms reboiler and withdrawing a third residue therefrom comprising water; and
    recovering an ethanol product from the overhead;
    wherein the intermediate reboiler is operated under non-esterification conditions, wherein less than 1000 ppm of ethyl acetate is formed in the intermediate reboiler.

18. The process of claim 17, wherein the intermediate reboiler supplies from 5 to 60% of total heat to the distillation column.

* * * * *